US007745547B1

(12) United States Patent
Auerbach et al.

(10) Patent No.: US 7,745,547 B1
(45) Date of Patent: Jun. 29, 2010

(54) MULTI-ARM CYCLIC OR CUBIC SILOXANE-BASED FORMULATIONS FOR DRUG DELIVERY

(75) Inventors: Andrew Auerbach, Livingston, NJ (US); Bhanu P. S. Chauhan, Staten Island, NY (US); Richard P. Clarke, Raleigh, NC (US); M. Ishaq Haider, Cary, NC (US); Umar Latif, Staten Island, NY (US)

(73) Assignees: Becton, Dickinson and Company, Franklin Lakes, NJ (US); Research Foundation of the City University of NY, New York, NY (US)

( * ) Notice: Subject to any disclaimer, the term of this patent is extended or adjusted under 35 U.S.C. 154(b) by 859 days.

(21) Appl. No.: 11/500,175

(22) Filed: Aug. 7, 2006

Related U.S. Application Data

(60) Provisional application No. 60/705,734, filed on Aug. 5, 2005.

(51) Int. Cl.
*C08L 73/00* (2006.01)
(52) U.S. Cl. .......................... 525/409; 524/588; 528/10
(58) Field of Classification Search .................. 514/63, 514/740, 579; 424/450, 484, 486; 428/402.2; 556/434, 450, 462, 464, 465, 467; 528/10–31, 528/33, 37; 525/409; 524/588
See application file for complete search history.

(56) References Cited

U.S. PATENT DOCUMENTS

| 5,443,747 | A  | * | 8/1995 | Inada et al. | 134/1 |
| 6,528,584 | B2 | * | 3/2003 | Kennedy et al. | 525/101 |
| 6,660,822 | B2 | * | 12/2003 | Lyu et al. | 528/35 |
| 2003/0232944 | A1 | * | 12/2003 | Molenberg et al. | 528/10 |
| 2005/0090607 | A1 | * | 4/2005 | Tapsak et al. | 524/588 |

FOREIGN PATENT DOCUMENTS

EP    1074244  A2  *  7/2001

* cited by examiner

*Primary Examiner*—Randy Gulakowski
*Assistant Examiner*—Alicia M Toscano
(74) *Attorney, Agent, or Firm*—Alston & Bird LLP

(57) ABSTRACT

The present invention provides multi-arm siloxane-based molecules suitable for use as a drug delivery vehicle comprising a central core molecule that comprises a cyclic or cubic siloxane, and a plurality of arms attached to the central core molecule, wherein each arm comprises an organic moiety. The multi-arm siloxane-based molecules described herein are suitable for encapsulation of a therapeutic agent. The invention further includes pharmaceutical compositions comprising the claimed multi-arm siloxane-based molecules and an encapsulated therapeutic agent in combination with a pharmaceutically acceptable carrier. Methods of making and using the multi-arm siloxane-based molecules are also provided.

20 Claims, 7 Drawing Sheets

A

B

C

B

A

MULTI-ARM CYCLIC OR CUBIC SILOXANE-BASED FORMULATIONS FOR DRUG DELIVERY

CROSS-REFERENCE TO RELATED APPLICATIONS

This application claims the benefit of U.S. Provisional Patent Application No. 60/705,734, filed Aug. 5, 2005, which is herein incorporated by reference in its entirety.

FIELD OF THE INVENTION

The present invention relates to multi-arm siloxane-based molecules suitable for use as a drug delivery vehicle having a central core molecule comprising a cubic or cyclic siloxane, and a plurality of arms attached to the central core molecule, wherein each arm comprises an organic moiety.

BACKGROUND OF THE INVENTION

Drug discovery recently has experienced tremendous growth, facilitated in part by novel technologies, such as combinatorial chemistry and high-throughput screening. These novel approaches have led to drugs that generally are more potent and have better solubility and activity profiles than drugs developed from traditional approaches of medicinal chemistry. The discovery of such drugs has resulted in a more urgent focus on developing novel techniques to deliver these drugs more effectively, efficiently, and safely.

The conventional oral and intravenous routes of drug administration do not provide ideal pharmacokinetic profiles, especially for drugs that display high toxicity and/or narrow therapeutic windows. For such drugs the ideal pharmacokinetic profile would be one wherein the drug concentration reaches therapeutic levels without exceeding the maximum tolerable dose and maintains these concentrations for extended periods of time until the desired therapeutic effect is reached. One approach for achieving such a profile is encapsulating the drug in a polymer matrix.

Although efforts have been made to develop suitable polymer matrices for drug delivery, there remains a need in the art for compositions and methods for therapeutically effective and safe delivery of a drug to a subject. Compositions and methods that provide for drug delivery on demand, localized drug delivery, sustained or controlled-release of a drug, or improved drug stability are particularly advantageous.

BRIEF SUMMARY OF THE INVENTION

The present invention is directed to multi-arm siloxane-based molecules useful as drug delivery vehicles. The multi-arm siloxane-based molecules comprise a central core molecule comprising a cyclic or cubic siloxane, and a plurality of arms attached to the central core molecule, each arm comprising an organic moiety. The multi-arm siloxane-based molecules described herein may further comprise one or more encapsulated therapeutic agents. Pharmaceutical compositions comprising a multi-arm siloxane-based molecule of the invention having a therapeutic agent encapsulated therein and a pharmaceutically acceptable carrier are also provided. Accordingly, the compositions of the invention find use in the delivery of a therapeutic agent to a subject and may permit localized, slow, sustained, or controlled-release of a therapeutic agent of interest.

DETAILED DESCRIPTION OF THE INVENTION

Figure 1:
FIG. 1 provides transmission electron microscopy images of the multi-arm siloxane-based molecule $(PEG400)_4D_4^M$ at 1 micron (A) and 50 nm (B). Experimental details are provided in Example 2.
Figure 1:
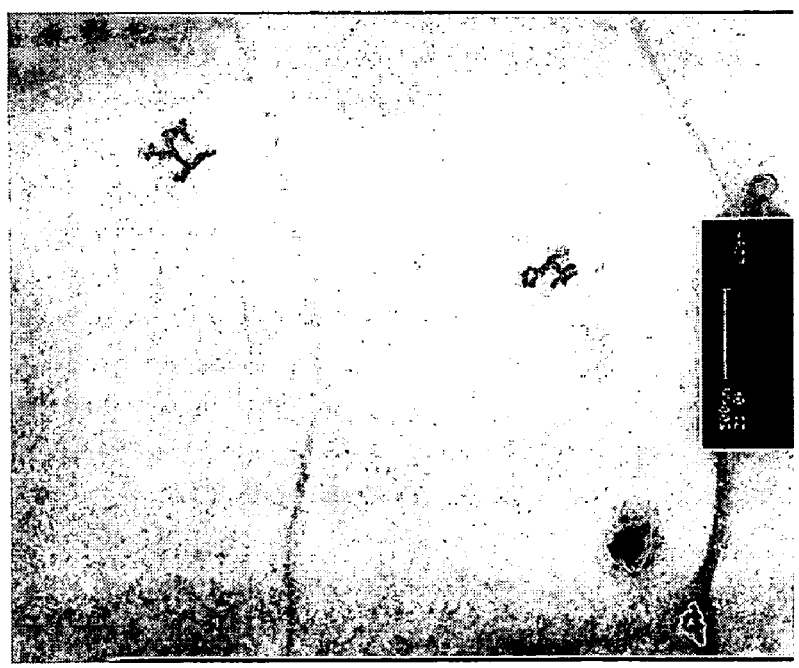

The presently disclosed subject matter now will be described more fully hereinafter with reference to the accompanying drawings, in which some, but not all embodiments of the presently disclosed subject matter are shown. Indeed, the presently disclosed subject matter may be embodied in many different forms and should not be construed as limited to the embodiments set forth herein; rather, these embodiments are provided so that this disclosure will satisfy applicable legal requirements.

Many modifications and other embodiments of the presently disclosed subject matter set forth herein will come to mind to one skilled in the art to which the presently disclosed subject matter pertain having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The present invention is directed to multi-arm siloxane-based molecules suitable for use as drug delivery vehicles. As used herein, the term "multi-arm siloxane-based molecule" refers to any siloxane molecule that has been chemically modified to comprise a plurality of arms radially attached (e.g., covalently attached) to a central core siloxane molecule, with each arm comprising the same or a different organic moiety. In one aspect, a multi-arm siloxane-based molecule is provided comprising a central core molecule that comprises a cyclic or cubic siloxane, and a plurality of arms attached to the central core molecule, each of the arms comprising an organic moiety. In particular embodiments, the arms are covalently attached to the central core molecule and comprise hydrophilic organic moieties, such as poly(ethylene glycol) (PEG) molecules, as described in greater detail herein below. Compositions comprising a plurality of the multi-arm siloxane-based molecules of the invention are also provided.

In certain aspects, a therapeutic agent (e.g., a drug) is encapsulated within a multi-arm siloxane-based molecule. "Encapsulation" is intended to refer to the physical confinement of a therapeutic agent within a multi-arm siloxane-based molecule. The therapeutic agent may be encapsulated within the central core molecule, the organic moiety arms, or both. Furthermore, when a plurality of multi-arm-siloxane-based molecules is present, the therapeutic agent may be encapsulated or entrapped within one or more layers between the multi-arm siloxane-based molecules. Encapsulation typically does not require or involve covalent attachment of the therapeutic agent to the multi-arm siloxane-based molecule, and thereby permits the release of the encapsulated therapeutic agent, particularly into the bloodstream of a subject, under appropriate conditions. Encapsulation of therapeutic agents of particular interest is described below in the Experimental section. Accordingly, the multi-arm siloxane-based molecules of the invention are useful as drug delivery vehicles.

The term "therapeutic agent" generally refers to any compound or composition that is intended to treat, cure, or prevent a disease, condition, or symptoms thereof in a subject (e.g., human or non-human animals). "Therapeutic agent" and "drug" may be used herein interchangeably. Any therapeutic agent, or combination of therapeutic agents, can be used in the practice of the invention, including but not limited to, anti-cancer agents, diabetes-controlling agents, antibiotics, antifungal agents, antiviral agents, anti-inflammatory drugs, migraine drugs, anti-anxiety agents, hormones, growth factors, steroidal agents, cardiovascular agents, and the like. In particular embodiments, an anticancer drug, such as cisplatin, paclitaxel, or cytoxan, a diabetes-controlling agent (e.g., insulin), or a migraine drug (e.g., sumatriptan) is encapsulated in a multi-arm siloxane-based molecule of the invention. In a further aspect of the invention, two or more therapeutic agents, such as, for example, paclitaxel and cisplatin, are encapsulated in a multi-arm siloxane-based molecule. The encapsulation of two or more therapeutic agents may permit concurrent or sequential release of the encapsulated agents in a subject.

The encapsulated therapeutic agent may be utilized per se or in the form of a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

As used herein, "drug delivery vehicle" or "delivery vehicle" is intended to mean a composition capable of encapsulating a therapeutic agent and subsequently releasing the agent at, for example, a particular time or at a specified location within the body of a subject. Accordingly, compositions comprising the multi-arm siloxane-based molecules of the invention may also be referred to herein as "drug delivery vehicles" or "delivery vehicles." These drug delivery vehicles may be designed such that drug delivery on demand (e.g., release of the therapeutic agent into the bloodstream in response to a specific cue) is accomplished. The cue for release of the encapsulated therapeutic agent from the multi-arm siloxane-based molecules of the invention may involve delivery of an acidic, basic, or novel catalyst (e.g., by pressure activation of breakable microcapsules containing a catalyst or by delivery of a catalyst through a patch, chip, or injection) to break up the multi-arm siloxane-based molecules. One of skill in the art will also recognize that a drug delivery vehicle of the invention comprising a claimed multi-arm siloxane-based molecule may be designed to permit: localized delivery of a therapeutic agent to avoid systemic exposure to a drug; sustained delivery of drugs to avoid multiple administrations and increase patient compliance; and stabilization of the drug to protect it from detrimental physiological conditions.

In some embodiments, it may be desirable to covalently attach a targeting moiety to the multi-arm siloxane-based molecule. As used herein, "targeting moiety" includes any chemical moiety capable of binding to, or otherwise exhibiting an affinity for, a particular type of tissue or component thereof. The addition of a targeting moiety to the multi-arm siloxane-based molecule can direct the molecule to particular sites within the body of a subject for targeted release of the encapsulated drug. For example, certain moieties are known to exhibit an affinity for hydroxyapatite surfaces (i.e. calcium phosphate), such as bone. Exemplary hydroxyapatite-targeting moieties include tetracycline, calcein, bisphosphonates, such as 4-amino-1-hydroxybutane-1,1-diphosphonic acid, ditetrabutylammonium salt (AHBDP) or derivatives thereof, polyaspartic acid, polyglutamic acid, and aminophosphosugars. Additional targeting moieties include proteins, antibodies, antibody fragments, peptides, carbohydrates, lipids, oligonucleotides, DNA, RNA, or small molecules.

The drug delivery vehicles disclosed herein also may be implanted directly at the site where drug action is needed, thereby reducing systemic exposure of the drug. This capability can be especially important for toxic drugs (such as the chemotherapeutic drugs), which result in various systemic side effects. Further, in some embodiments, the presently disclosed drug encapsulated delivery vehicles can be implanted into a tissue of interest, such as a tumor, for sustained and controlled drug delivery. In the same manner, a targeting moiety (e.g., an antibody) can be used to target the chemotherapeutic agent to the tumor. Such antibodies, for example, specifically bind to the surface of cancer cells.

Compositions comprising a plurality of the multi-arm siloxane-based molecules of the invention, particularly in a solution, are also encompassed by the present invention. While not intending to be limited to a particular mechanism, it is hypothesized that by attaching hydrophilic organic arms such as PEG molecules to a hydrophobic cyclic or cubic siloxane (i.e., the central core molecule), hybrid networks may be formed that can self-assemble into micellar structures of varying sizes and formats (e.g., micro/nano-spheres, a gel, a film or an extruded shape, such as cylinder or cylinder). For example, the micellar structures may be from about 15 nm to about 5 microns, particularly about 20 nm to about 1 micron, more particularly about 25 nm to about 500 nm in size. Aggregates comprising a drug delivery vehicle and an encapsulated drug may be on the order of about 1 micron to about 5 microns. Such micellar structures may be useful for drug delivery to a subject and may permit drug delivery on demand, localized drug delivery, sustained-release of a drug, and/or stabilization of a drug. Therapeutic agents encapsulated in a multi-arm siloxane-based molecule of the invention would be less likely to release the entrapped molecule at an undesirably rapid rate.

The shape and size of the resulting multi-arm siloxane-based micellar structures may be important in, for example, drug delivery kinetics. For example, the solubility properties of multi-arm siloxane-based molecules comprising PEG arms lead to soluble, processable and tractable architectures providing well-defined cavities for drug delivery applications. The skilled artisan would further recognize that varying the length of the arms (e.g. PEG arms), the end cap present on the arms, the silicon to oxygen linkage on the reacting organic moiety arm, and the size of the cyclic or cubic ring would modify the time and rate of release of the drug.

The Central Core Molecule

The central core molecule of the compositions of the invention comprises a siloxane molecule that provides a number of attachment sites equal to the number of desired organic moiety arms. The central core siloxane molecules will typically comprise 3 to 10 arm attachment sites, more particularly 4 to 8 arm attachment sites. Siloxane molecules are known in the art and are a class of hydrophobic organosilicon compounds comprising silicon, oxygen, and alkane molecules. Siloxanes suitable for use in the invention comprise cyclic or cubic siloxanes, particularly poly methyl hydrosiloxanes (PMHS) which contain an active hydrogen, including but not limited to tetramethylcyclotetrasiloxane ("$D_4$"), pentamethycyclopentasiloxane ("$D_5$"), and octakis(dimethylsiloxy)-silsesquioxane ("$T_8$"). The choice of organopolysiloxanes can be characterized by the combination of chemical, mechanical and electrical properties, which taken together are not common to any other class of well-defined polymers. Cyclic siloxanes possess a well-defined cavity size which makes them particularly suited for use as drug delivery vehicles. Any cyclic or cubic siloxane that can be modified to comprise a plurality of arms attached to and radiating from the central siloxane molecule may be used in the practice of the present invention.

The Organic Moiety Arm Molecules

As described above, the multi-arm siloxane-based molecules of the invention comprise a central core molecule (i.e., a cyclic or cubic siloxane), and a plurality of arms attached to the central core molecule, wherein each arm comprises an organic moiety. Any organic moiety capable of attaching to the central core siloxane molecule that further imparts the desired properties to the multi-arm siloxane-based molecule (e.g., drug encapsulation and delivery capabilities) may be used in the practice of the invention. The arms will generally comprise organic moieties that are nontoxic and biocompatible, meaning that the moiety is capable of coexistence with living tissues or organism without causing harm. In certain aspects, the arms comprise hydrophilic organic molecules, more preferably hydrophilic polymers. In particular embodiments, the arms attached to the central siloxane molecule comprise a poly(ethylene glycol) (PEG). The term PEG includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In its simplest form, PEG has the formula —$CH_2CH_2O$—($CH_2CH_2O)_n$—$CH_2CH_2$—, where n is from about 10 to about 4000, typically from about 20 to about 500. PEGs having a number average molecular weight of from about 400 Da to about 100,000 Da, particularly about 300 Da to about 1500 Da, more particularly about 400 Da to about 1000 Da are useful as a hydrophilic polymer arm. For example, PEG polymer arms having a molecular weight of about 400 Da or about 1000 Da are useful in the present invention. The length of the PEG arm may be varied as needed. Numerous PEGs are known in the art and are commercially available.

In one form useful in the present invention, free or non-bound PEG is a linear polymer terminated at each end with hydroxyl groups:

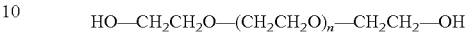

The above polymer, alpha-,omega-dihydroxylpoly(ethylene glycol), can be represented in brief form as HO-PEG-OH where it is understood that the -PEG- symbol represents the following structural unit:

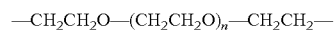

where n typically ranges from about 10 to about 4000.

Another type of PEG useful in forming the conjugates of the invention is methoxy-PEG-OH, or mPEG in brief, in which one terminus is the relatively inert methoxy group, while the other terminus is a hydroxyl group that is subject to ready chemical modification. The structure of mPEG is given below.

where n is as described above.

Multi-armed or branched PEG molecules, such as those described in U.S. Pat. No. 5,932,462, which is incorporated by reference herein in its entirety, can also be used as a hydrophilic PEG polymer arm. For example, the hydrophilic PEG segment can have the structure:

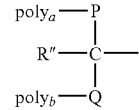

Formula I wherein:

$poly_a$ and $poly_b$ are PEG backbones, such as methoxy poly (ethylene glycol);

R" is a nonreactive moiety, such as H, methyl or a PEG backbone; and

P and Q are nonreactive linkages.

The PEG polymer may alternatively comprise a forked PEG. An example of a forked PEG is represented by PEG-YCHZ$_2$, where Y is a linking group and Z is an activated terminal group linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG segment rather than at the end of the PEG chain. The pendant reactive groups can be attached to the PEG segment directly or through a linking moiety, such as alkylene.

In addition to the above-described forms of PEG, the polymer can also be prepared with one or more weak or degradable linkages in the segment, including any of the above described polymers. For example, PEG can be prepared with ester linkages in the polymer segment that are subject to hydrolysis. As shown below, this hydrolysis results in cleavage of the polymer into fragments of lower molecular weight:

Similarly, the PEG polymer can be covalently attached to the hydrophobic polymer segment or other molecules through a weak or degradable linkage moiety.

Other hydrolytically degradable linkages, useful as either a degradable linkage within a polymer segment or as a degradable linkage connecting the PEG polymer to other molecules include carbonate linkages; imine linkages resulting, for example, from reaction of an amine and an aldehyde (see, e.g., Ouchi et al., *Polymer Preprints*, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

The term "PEG" further includes such molecules as, for example, poly(ethylene glycol) tetrahydrofurfuryl ether and poly(ethylene glycol) methyl ether (e.g., with molecular weights of about 350 to about 550).

It is understood by those skilled in the art that the term poly(etylene glycol) or PEG represents or includes all the above forms of PEG. One of skill in the art will appreciate that in addition to the various PEG molecules described above, other organic moieties can be used as the arms of the compositions of the invention, including but not limited to diethylene glycol, butoxyethanol, and decylalcohol.

The skilled artisan will recognize that the presently disclosed multi-arm siloxane-based molecules can be modified to control the time and rate of release of an encapsulated drug. Such modifications can include, but are not limited to, varying the length of the PEG arms; varying the end cap on the PEG; varying the sulfur (S) to oxygen (O) linkage on the reacting PEG moiety; and changing the size of the siloxane ring.

Although the specific examples of multi-arm siloxane-based molecules in the appended Experimental section utilize the same organic moiety for each arm, it is possible to utilize different organic moieties within the same multi-arm siloxane-based molecule. In other words, the present invention includes embodiments wherein more than one organic moiety combination, particularly a combination of hydrophilic polymers, is attached to the same central core molecule.

The PEG polymer arms of the claimed multi-arm siloxane-based molecules may further include one or more capping groups covalently attached to the PEG molecule, such as at a terminus of the PEG segment distal from the point of attachment to the central core siloxane molecule. The capping group can be a relatively inert group, such as an alkoxy group (e.g. methoxy or ethoxy). Alternatively, the capping group can be a reactive functional group, such as a functional group capable of reacting with a targeting moiety or drug molecule so that such molecules can be attached to the PEG polymer as described above. Exemplary functional groups, optionally in protected form, include hydroxyl, protected hydroxyl, active ester (e.g. N-hydroxysuccinimidyl, 1-benzotriazolyl, p-nitrophenyl, or imidazolyl esters), active carbonate (e.g. N-hydroxysuccinimidyl, 1-benzotriazolyl, p-nitrophenyl, or imidazolyl carbonate), acetal, aldehyde, aldehyde hydrates, alkyl or aryl sulfonate, halide, disulfide derivatives such as o-pyridyl disulfidyl, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, or tresylate.

As would be understood in the art, the term "protected" refers to the presence of a protecting group or moiety that prevents reaction of the chemically reactive functional group under certain reaction conditions. The protecting group will vary depending on the type of chemically reactive group being protected and the reaction conditions employed. For example, if the chemically reactive group is an amine or a hydrazide, the protecting group can be selected from the group of tert-butyloxycarbonyl (t-Boc) and 9-fluorenyl-methoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention, see for example, Greene, T. W., et al., *Protective Groups In Organic Synthesis*, 2nd ed., John Wiley & Sons, New York, N.Y. (1991).

Specific examples of functional groups for the hydrophilic polymer arms of the invention include but are not limited to N-succinimidyl carbonate (see e.g., U.S. Pat. Nos. 5,281,698, 5,468,478), amine (see, e.g., Buckmann et al. *Makromol. Chem.* 182:1379 (1981), Zaplipsky et al. *Eur. Polym. J.* 19:1177 (1983)), hydrazide (See, e.g., Andresz et al. *Makromol. Chem.* 179:301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. *Cancer Biochem. Biophys.* 7:175 (1984) and Joppich et al. *Macrolol Chem.* 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g., Beauchamp, et al., *Anal. Biochem.* 131:25 (1983), Tondelli et al. *J. Controlled Release* 1:251 (1985)), p-nitrophenyl carbonate (see, e.g., Veronese, et al., *Appl. Biochem. Biotech.*, 11:141 (1985); and Sartore et al., *Appl. Biochem. Biotech.*, 27:45 (1991)), aldehyde (see, e.g., Harris et al. *J. Polym. Sci. Chem.* Ed. 22:341 (1984), U.S. Pat. No. 5,824,784, U.S. Pat. No. 5,252,714), maleimide (see, e.g., Goodson et al. *Bio/Technology* 8:343 (1990), Romani et al. in Chemistry of Peptides and Proteins 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules*, 26:581 (1993)), vinylsulfone (see, e.g., U.S. Pat. No. 5,900, 461). All of the above references are incorporated herein by reference.

One of skill in the art would recognize that varying the end cap present on a PEG polymer arm may also alter the rate of release of a therapeutic agent encapsulated within a multi-arm siloxane-based molecule of the invention.

Methods of Making the Multi-Arm Siloxane-Based Molecules

Exemplary methods for preparing the multi-arm siloxane-based molecules of the invention are provided herein below and in the Experimental section. For example, the generation of covalently attached PEG arms to a central cyclic or cubic siloxane molecule may be accomplished by "Chauhan-Boudjouk alcoholysis," which can provide a one-step process to selective formation of PEG-substituted cyclic siloxanes. See, for example, Chauhan et al. (2001) *Organometallics* 20:2725; Boudjouk et al. U.S. Pat. No. 6,482,912 (2002); Ready et al. (2001) *Macromol. Rapid Commun.* 22:654; and Boudjouk et al. (2004) *J. Organomet. Chem.* 689:3468, all of which are herein incorporated by reference in their entirety. This procedure is a route for selective modification of Si—H bonds and leads to quantitative yields of the desired products. Another advantage of this strategy is that it is compatible with variety of functional groups. Briefly, the cyclic or cubic siloxane is reacted with the PEG of interest in the presence of Wilkinson's catalyst ($RhCl(PPh_3)_3$) in benzene under positive pressure and with subsequent heating of the reaction mixture. Synthesis of the desired multi-arm siloxane-based molecule can be monitored by, for example, IR spectral analysis, $^1H$ NMR, $^{29}Si$ NMR, transmission electron microscopy (TEM), and other analytical techniques well known in the art.

One of skill in the art will appreciate that other methods for synthesizing the multi-arm siloxane-based molecules of the invention beyond those described herein may be utilized to produce the desired products.

Exemplary Multi-Arm Siloxane-Based Molecules

More specific structural embodiments of the multi-arm siloxane-based molecules of the invention, as well as schemes for the synthesis of these exemplary molecules, will now be described here and below in the Experimental section. The specific structures shown below are presented as exemplary structures only and are not intended to limit the scope of the invention.

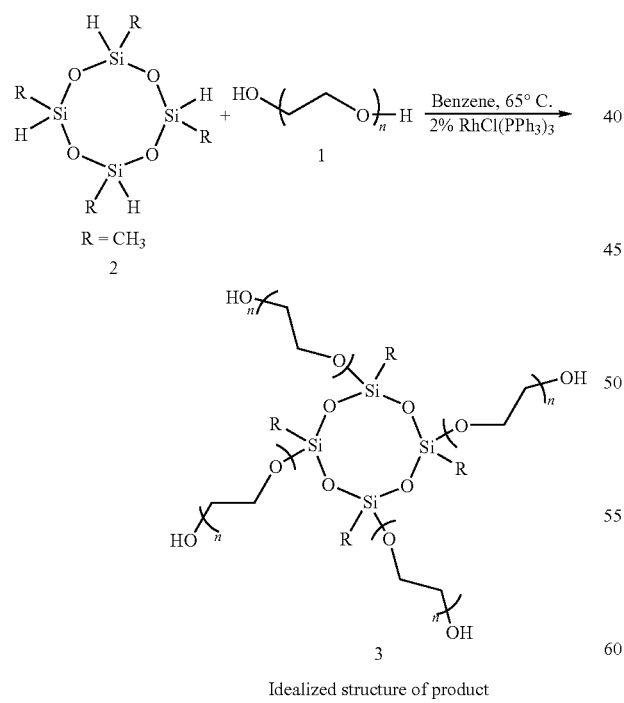

Idealized structure of product wherein; structure 2 is tetramethylcyclotetrasiloxane $D_4^H$;
structure 1 is PEG 400 (molecular weight (MW) 400); and
structure 3 is $(PEG400)_4D_4^M$.

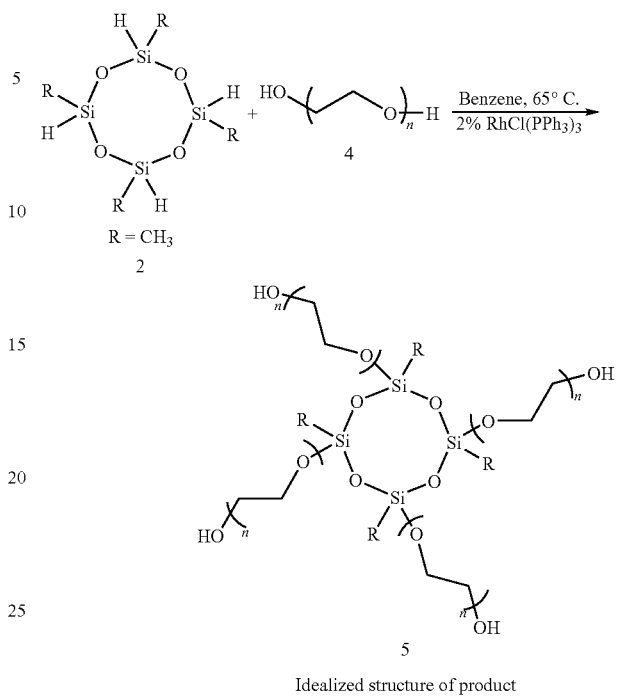

Idealized structure of product wherein structure 2 is tetramethylcyclotetrasiloxane $D_4^H$;
structure 4 is PEG 1000 (MW 1000); and
structure 5 is $(PEG1000)_4D_4^M$.

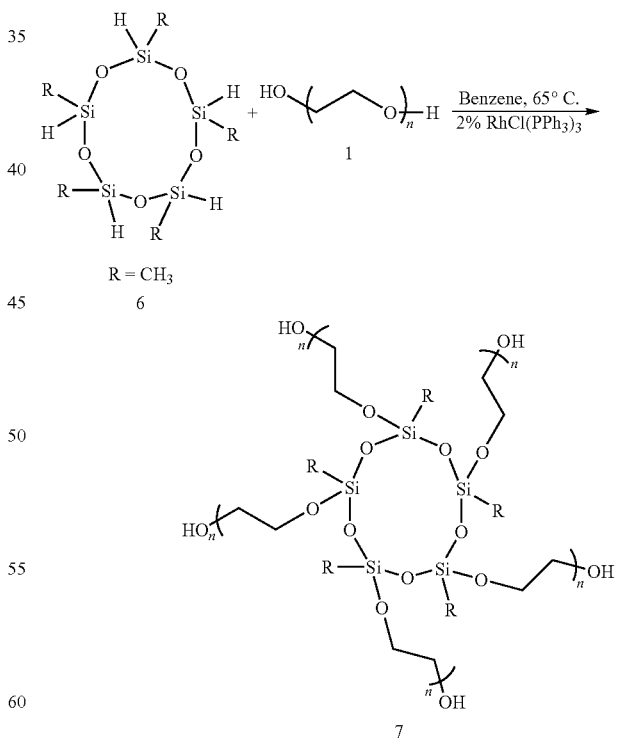

Idealized structure of product wherein structure 6 is pentamethycyclopentasiloxane $D_5^H$;
structure 1 is PEG 400 (molecular weight (MW) 400); and
structure 7 is $(PEG400)_5D_5^M$.

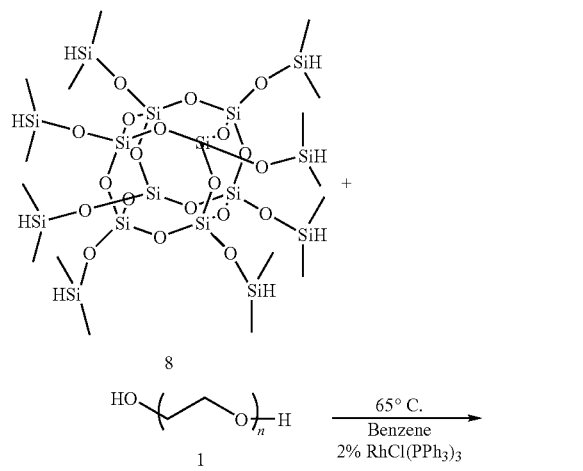

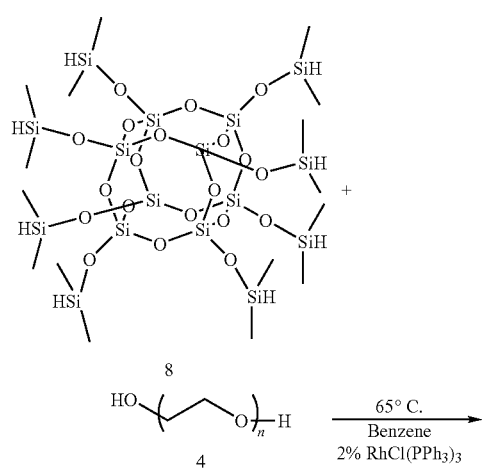

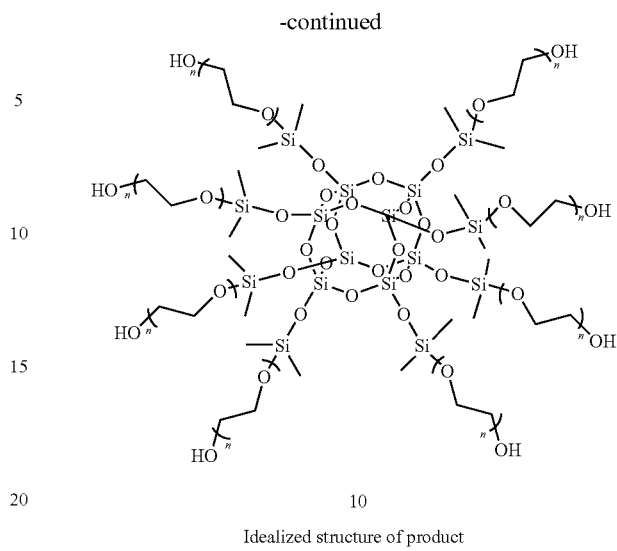

wherein structure 8 is octakis(dimethylsiloxy)-T8-silsesquioxane ($T_8$);
wherein structure 1 is PEG 400 (molecular weight (MW) 400); and
structure 9 is $(PEG400)_8T_8$.

wherein structure 8 is octakis(dimethylsiloxy)-T8-silsesquioxane ($T_8$);
structure 4 is PEG 1000 (MW 1000); and
structure 10 is $(PEG1000)_8T_8$.

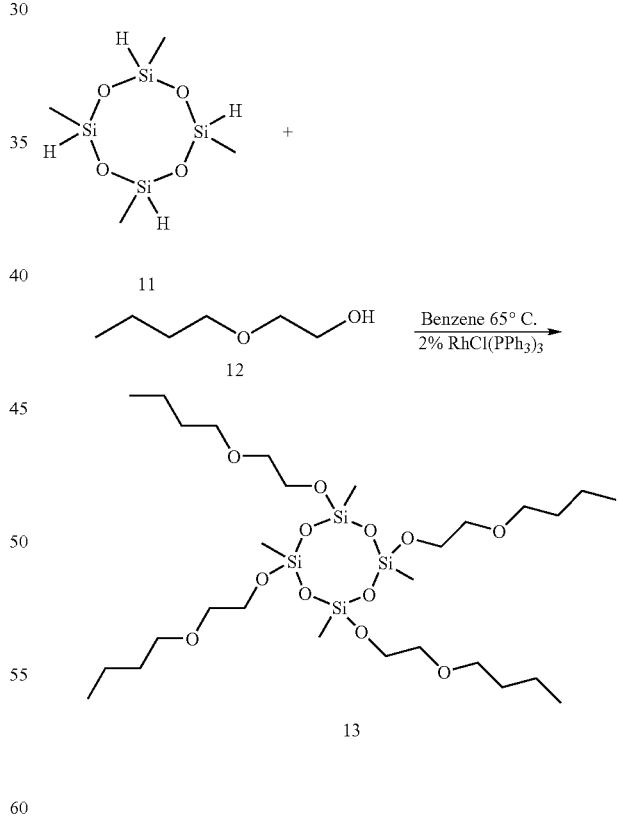

wherein structure 11 is tetramethylcyclotetrasiloxane $D_4^H$;
structure 12 is poly(ethylene glycol) tetrahydrofurfuryl; and
structure 13 is poly(ethylene glycol) tetrahydrofurfuryl ether substituted $D_4$ (also referred to as (PEG-THF ether)$_4$ $D_4^{M_1}$).

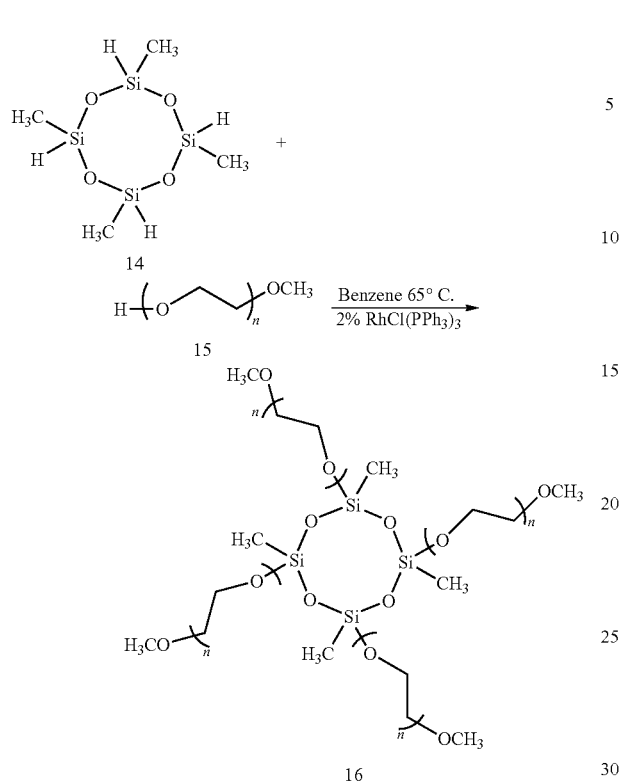

wherein structure 14 is tetramethylcyclotetrasiloxane $D_4^H$;
structure 15 is decylalcohol; and
structure 16 is decylalcohol substituted $D_4$ ($DA_4D_4^M$).

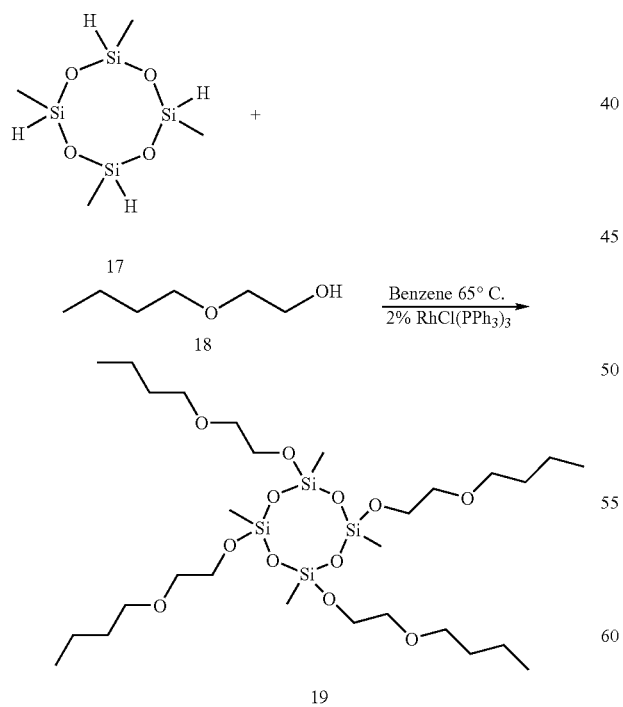

wherein structure 17 is tetramethylcyclotetrasiloxane $D_4^H$;
structure 18 is butoxyethanol; and
structure 19 is butoxyethanol substituted $D_4$ ($BE_4D_4^M$).

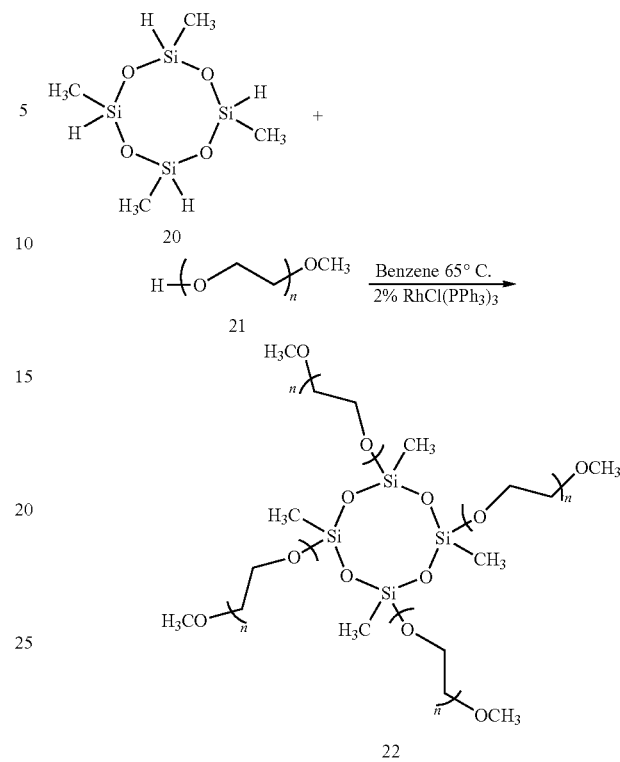

wherein structure 20 is tetramethylcyclotetrasiloxane $D_4^H$;
structure 21 is poly(ethylene glycol) methyl ether 350; and
structure 22 is poly(ethylene glycol) methyl ether 350 substituted $D_4$ (also referred to as $[PEGMetEt(350)]_4D_4^M$ or $(PME350)_4D_4$).

wherein structure 23 is tetramethylcyclotetrasiloxane $D_4^H$;

structure 24 is poly(ethylene glycol) methyl ether 550; and structure 25 is poly(ethylene glycol) methyl ether 550 substituted $D_4$ (also referred to as $[PEGMetEt(550)]_4D_4^M$ or $(PME550)_4D_4$).

Pharmaceutical Compositions Comprising the Multi-Arm Siloxane-Based Molecules

In another aspect, the invention provides pharmaceutical formulations or compositions, both for veterinary and for human medical use, comprising a multi-arm siloxane molecule as described above, at least one therapeutic agent entrapped therein, and typically a pharmaceutically acceptable carrier. The pharmaceutical formulation may include one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), and in "Handbook of Pharmaceutical Excipients", Third Ed., Ed. A. H. Kibbe, Pharmaceutical Press, 2000.

The multi-arm siloxane-based molecules of the invention may be formulated in compositions including those suitable for oral, buccal, rectal, topical, nasal, ophthalmic, or parenteral (including intradermal implantation, intradermal injection, intraperitoneal, intravenous, subcutaneous, or intramuscular injection) administration. The multi-arm siloxane-based molecules may also be used in formulations suitable for inhalation. The compositions may conveniently be presented in unit dosage form and may be prepared by any of the methods well known in the art of pharmacy. All methods include the step of bringing the claimed molecules with drug encapsulated therein into association with a carrier that constitutes one or more accessory ingredients. In general, the compositions are prepared by bringing the multi-arm siloxane-based molecule/therapeutic agent composition into association with a liquid carrier to form a solution or a suspension, or alternatively, bringing the multi-arm siloxane-based molecule/therapeutic agent composition into association with formulation components suitable for forming a solid, optionally a particulate product, and then, if warranted, shaping the product into a desired delivery form.

The amount of the therapeutic agent or drug in the formulation will vary depending upon the specific drug employed, its molecular weight, and other factors such as dosage form, target patient population, and other considerations, and will generally be readily determined by one skilled in the art. The amount of therapeutic agent in the formulation will be that amount necessary to deliver a therapeutically effective amount of the drug to a patient in need thereof to achieve at least one of the therapeutic effects associated with the drug. In practice, this will vary widely depending upon the particular drug, its activity, the severity of the condition to be treated, the patient population, the stability of the formulation, and the like. Generally a "therapeutically effective amount or dose" is an amount of a therapeutic agent that when administered to a subject brings about a positive therapeutic response with respect to the prevention or treatment of a particular disease or condition or the alleviation of symptoms associated therewith. For example, a therapeutically effective dose of paclitaxel typically ranges from about 1 mg/m$^2$ to about 250 mg/m$^2$, particularly about 10 mg/m$^2$ to about 150 mg/m$^2$, more particularly about 20 mg/m$^2$ to about 100 mg/m$^2$ (per IV cycle). Similarly, a typical therapeutically effective dose of cisplatin is in the range of about 5 mg/m$^2$ to about 300 mg/m$^2$, particularly about 50 mg/m$^2$ to about 200 mg/m$^2$, more particularly about 75 mg/m$^2$ to about 175 mg/m$^2$ (per IV cycle). A therapeutically effective amount of a therapeutic agent of the invention can be readily determined by one of ordinary skill in the art without undue experimentation.

Methods of Using the Multi-Arm Siloxane-Based Molecules

As noted above, one or more therapeutic agents can be encapsulated in the multi-arm siloxane-based molecules of the invention, and this complex further placed in a solution to form micellar structures. As a result, the multi-arm siloxane-based molecules of the invention may be used as drug delivery vehicles by encapsulating the therapeutic agent and administering a therapeutically effective amount of the multi-arm siloxane-based molecules with the therapeutic agent entrapped therein to a mammal.

The multi-arm siloxane-based molecules of the invention can be used as drug delivery vehicles for any condition responsive to a therapeutic agent capable of entrapment within the structure. Thus, the compositions of the invention can be used in pharmaceutical formulations useful for treating any condition responsive to a particular therapeutic agent in a subject, including a human. A preferred condition for treatment is cancer. The method of treatment comprises administering to the subject a therapeutically effective amount of a composition or formulation containing the multi-arm siloxane-based molecule with a therapeutic agent encapsulated therein as described above. The therapeutically effective dosage amount of any specific formulation will vary somewhat from drug to drug, patient to patient, and will depend upon factors such as the condition of the patient, the loading capacity of the block copolymer, and the route of delivery.

The multi-arm siloxane-based molecule/encapsulated therapeutic agent composition may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals. Possible routes of delivery include intradermal implantation, intradermal injection, buccally, subcutaneously, transdermally, intramuscularly, intravenously, orally, or by inhalation. The compositions of the invention may also permit less frequent dosing, such as, for example, once-weekly dosing.

Multi-Arm Siloxane-Based Molecules as Nanoreactors

The presently disclosed cyclic and cubic siloxanes also can be used as nano-reactors based on their unique specific geometry. See, for example, Chauhan and Latif (2005) *Macromolecules* 38:6231-6235 and Chauhan et al. (2005) *Acta Chim. Slov.* 52:361-370, both of which are herein incorporated by reference in their entirety. These materials can be tailored for specific assembly characteristics. The multi-arm cyclic and cubic siloxanes, e.g., $[R_2SiO_2]_4$ or $[RSiO_3]_8$, offer the opportunity to develop a wide range of hybrid materials. Due to their specific assembly characteristics, such siloxanes can be tailored as new and interesting classes of macromolecules having controlled architectures. Catalytic routes for selective modification of multi Si-centers can lead to covalently-linked organic functional groups, which in turn can lead to libraries of inorganic/organic hybrids. See, e.g., Huang et al. (2004) *Langmuir* 20:5145; Choi et al. (2001) *J. Am. Chem. Soc.* 123:11420; Lain et al. (1998) *App. Organometal. Chem.* 12:715; Knischka et al. (1999) *Langmuir* 15:4752; and Lichtenhan et al. (1993) *Macromolecules* 26: 2141, each of which is incorporated herein by reference in their entirety. Moreover, the presently disclosed controlled synthetic route also allows for a detailed and more general examination of the effects of variations on interfacial interactions on hybrid properties.

In particular embodiments, a metal group (e.g., a silver or palladium molecule), rather than a therapeutic agent as described above, is encapsulated in a multi-arm siloxane-based molecule of the invention. Such metal-containing nanoreactors find use, for example, as sensors for medical diagnostic techniques.

The article "a" and "an" are used herein to refer to one or more than one (i.e., at least one) of the grammatical object of an article. By way of example, "an element" means one or more elements.

Throughout the specification and claims the word "comprising," or variations thereof will be understood to imply the inclusion of a stated element, integer or step, or group of elements, integers, or steps, but not the exclusion of any other element, integer or step, or group of elements, integers, or steps.

The following examples are offered by way of illustration and not by way of limitation.

EXPERIMENTAL

Example 1

Synthesis of Multi-Arm Siloxane-based Molecules (i.e., Drug Delivery Vehicles)

Methods for preparing exemplary drug delivery vehicles of the invention are provided below. In particular, vehicles were synthesized with varying sizes of siloxanes (cyclic $D_4$ $D_5$, cubic $T_8$) and with varying chain lengths of PEG (i.e., molecular weight (MW) 400 or 1000 Da). The synthetic procedures and analyses are described below.

A. Synthesis of Delivery Vehicle $(PEG400)_4D_4^M$

The delivery vehicle $(PEG400)_4D_4^M$ was prepared by adding Wilkinson's catalyst (0.002 g, 0.002 mmol) to a 50 mL Schlenk tube equipped with a magnetic stirring bar. The Schlenk tube was degassed and filled with nitrogen three times prior to the addition of PEG (see structure 1 below; PEG MW 400 Da; 3.2 g, 8 mmol). The reaction mixture was allowed to stir for 5 min to obtain a homogenous suspension of catalyst in PEG. Solvent (Benzene, 5 mL) was added to the reaction mixture, which resulted in a brownish solution. Tetramethylcyclotetrasiloxane $D_4^H$ (see structure 2 below; 0.48 g, 2 mmol) was added to the reaction mixture. The reaction mixture immediately turned yellow and development of a gas (presumably. $H_2$) was observed. The flask was degassed and filled with nitrogen three more times, and the reaction was allowed to continue at 65° C. under a positive nitrogen pressure for 35 hrs. Upon completion, the reaction mixture was a dark brown viscous solution. The solvent was evaporated and the product was analyzed with $^1H$, $^{13}C$, and $^{29}Si$ NMR. Analysis confirmed the formation of the desired product $(PEG400)_4D_4^M$ (see structure 3 below). The synthetic reaction is shown in scheme 1.

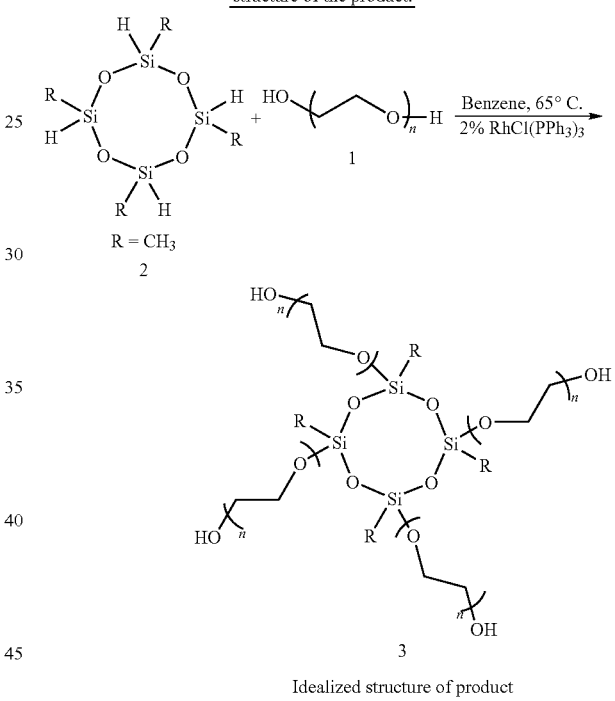

Scheme 1:
Synthetic route to PEG400 substituted cyclic siloxane and idealized structure of the product.

3

Idealized structure of product

The $^1H$, $^{13}C$, and $^{29}Si$ NMR data are summarized as follows: Yield: 98% $^1H$ NMR (δ, ppm): 0.082 (m), 3.475 (s), 3.532 (m), 3.591 (m), 3.779 (m); $^{13}C$ NMR (δ, ppm): −5.236 (m), 60.824 (s), 69.659 (s), 69.872 (s), 71.965 (s); $^{29}Si$ NMR (δ, ppm): −58.489 (m), −57.955 (m).

To separate the catalyst, the reaction mixture was placed in a 250 mL round bottom flask equipped with a magnetic stirring bar. Approximately 30 mL of cyclohexane was added to the flask, and the solution was stirred vigorously for 10 min. Approximately 10 mL of water was added to the solution, producing a milky color solution. The solution was vigorously stirred for an additional 20 min and then collected in a separatory funnel and allowed to sit for one hour. The catalyst was separated at the interphase of both layers in form of precipitate. The bottom water layer containing the delivery vehicle was separated and centrifuged for 10 min at 9000 rpm to get rid of any traces of the catalyst. The water was evaporated in a rotary evaporator under vacuum at 95° C. for two hours. A clear viscous solution of the delivery vehicle (PEG400)$_4$D$_4^M$ resulted. The product was analyzed with $^1$H, $^{13}$C, and $^{29}$Si NMR again which showed a slight shift to upfield and a new small unidentified peak at ~−66 in $^{29}$Si NMR was observed, possibly the result of water treatment and formation of Si—OH bonds. The NMR data are as follows: Yield: 70% $^1$H NMR (δ, ppm): −0.315 (m), 3.121 (s), 3.185 (m), 3.230 (m), 3.652 (m); $^{13}$C NMR (δ, ppm): −4.318 (m), 60.468 (s), 69.348 (s), 69.591 (s), 71.836 (s); $^{29}$Si NMR (δ, ppm): −66.618 (m), −57.865 (m), −57.126 (m).

B. Synthesis of Delivery Vehicle (PEG1000)$_4$D$_4^M$

The delivery vehicle (PEG1000)$_4$D$_4^M$ was prepared by adding Wilkinson's catalyst (0.004 g, 0.004 mmol) to a 100 mL round bottom flask equipped with a vacuum inlet and a magnetic stirring bar. The flask was degassed and filled with nitrogen three times and then PEG (see structure 4 below; PEG MW 1000 Da; 8 g, 8 mmol). Solvent (Benzene, 15 mL) was added to the flask, and the reaction mixture was allowed to stir for 5 min, resulting in a brownish homogenous solution. Tetramethylcyclotetrasiloxane D$_4^H$ (see structure 2 below; 0.48 g, 2 mmol) was added to the reaction mixture. The reaction mixture immediately turned yellow and development of a gas (presumably H$_2$) was observed. The flask was degassed and filled with nitrogen three more times. The reaction was allowed to continue at 65° C. under a positive nitrogen pressure for 40 hrs. Upon completion, the reaction mixture was a dark brown viscous solution. The solvent was evaporated and the product was analyzed with $^1$H, $^{13}$C, and $^{29}$Si NMR, which confirmed the formation of desired product (PEG1000)$_4$D$_4^M$ (see structure 5 below). The synthetic reaction is shown in scheme 2.

Scheme 2:
Synthetic route to PEG1000 substituted cyclic siloxane and idealized structure of the product.

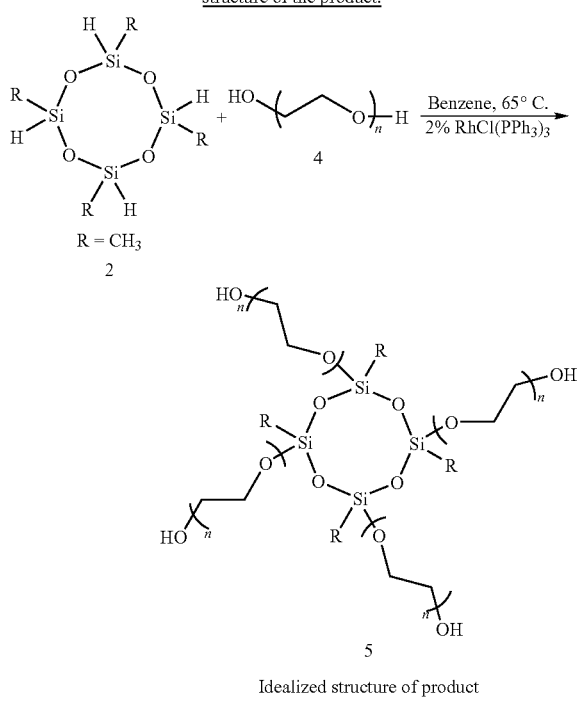

The $^1$H, $^{13}$C, and $^{29}$Si NMR data are as follows: Yield: 98% $^1$H NMR (δ, ppm): 0.065 (m), 3.264 (s), 3.380 (m), 3.514 (m), 3.633 (m); $^{13}$C NMR (δ, ppm): −4.310 (m), 60.066 (s), 69.037 (s), 69.250 (s), 71.510 (s); $^{29}$Si NMR (δ, ppm): −56.854 (m).

The catalyst was separated in a similar fashion as described above. Specifically, the reaction mixture was placed in a 250 mL round bottom flask equipped with a magnetic stirring bar. Approximately 30 mL cyclohexane was added to the flask, and the solution was stirred vigorously for 10 min. Approximately 10 mL of water was added and resulted in a milky color solution. This solution was vigorously stirred for an additional 20 min and then collected in a separatory funnel and allowed to sit for one hour. The catalyst was separated at the interphase of both layers in form of precipitate. The bottom water layer containing delivery vehicle was separated and centrifuged for 10 min at 9000 rpm to remove any traces of the catalyst. The water was evaporated in a rotary evaporator under vacuum at 95° C. for two hours. The resultant product was a clear waxy solid of delivery vehicle (PEG1000)$_4$D$_4^M$. The product was analyzed with $^1$H, $^{13}$C, and $^{29}$Si NMR again which showed a slight shift to upfield. The NMR data are as follows: Yield: 70% $^1$H NMR (δ, ppm): −0.215 (m), 3.225 (m), 3.288 (s), 3.332 (m), 3.455 (m); $^{13}$C NMR (δ, ppm): −5.425 (m), 60.733 (s), 69.598 (s), 69.818 (s), 71.942 (s); $^{29}$Si NMR (δ, ppm): −57.135 (m)

C. Synthesis of Delivery Vehicle (PEG400)$_5$D$_5^M$

The delivery vehicle (PEG400)$_5$D$_5^M$ was prepared by adding Wilkinson's catalyst (0.002 g, 0.002 mmol) to a 50 mL Schlenk tube equipped with a magnetic stirring bar. The Schlenk tube was degassed and filled with nitrogen three times prior to the addition of PEG (see structure 1 below; PEG MW 400 Da; 1.6 g, 4 mmol). The reaction mixture was allowed to stir for 5 min to produce a homogenous suspension of catalyst in PEG. Solvent (Benzene, 3 mL) was added, which resulted in a brownish solution. Pentamethycyclopentasiloxane D$_5^H$ (see structure 6 below; 0.3 g, 1 mmol) was added to the reaction mixture. The reaction mixture immediately turned yellow and development of a gas (presumably H$_2$) was observed. The flask was degassed and filled with nitrogen three more times. The reaction was allowed to continue at 65° C. under a positive nitrogen pressure for 30 hrs. Upon completion, the reaction mixture was a dark brown viscous solution. The solvent was evaporated and the product was analyzed with $^1$H, and $^{29}$Si NMR, which confirmed the formation of desired product (PEG400)$_5$D$_5^M$ (see structure 7 below). The synthetic reaction is shown in scheme 3.

Scheme 3:
Synthetic route to PEG400 substituted cyclic siloxane and idealized structure of the product.

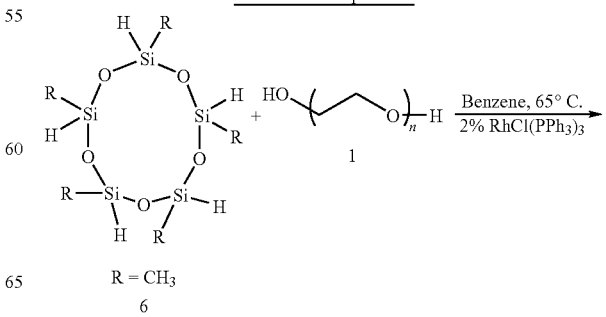

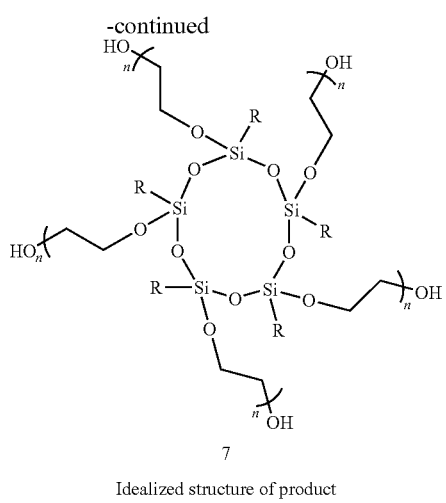

7

Idealized structure of product

The $^1$H, and $^{29}$Si NMR data are as follows: Yield: 98% $^1$H NMR (δ, ppm): 0.070 (m), 3.470 (m), 3.532 (s), 3.580 (m), 3.767 (m); $^{29}$Si NMR (δ, ppm): −58.860 (m), −59.296 (m).

The catalyst was separated in a similar fashion as described in preparation of (PEG400)$_4$D$_4^M$ above. In particular, the reaction mixture was placed in a 250 mL round bottom flask equipped with a magnetic stirring bar. Approximately 30 mL of cyclohexane was added to the flask, and the solution was stirred vigorously for 10. Approximately 10 mL of water was added, which resulted in a milky color solution. The solution was vigorously stirred for an additional 20 min and then collected in a separatory funnel and allowed to sit for one hour. The catalyst was separated at the interphase of both layers in form of precipitate. The bottom water layer containing delivery vehicle was separated and centrifuged for 10 min at 9000 rpm to remove any traces of the catalyst. The water was evaporated in a rotary evaporator under vacuum at 95° C. for two hours. The resultant product was a clear viscous solution of delivery vehicle (PEG400)$_5$D$_5^M$. The product was analyzed with $^1$H, $^{13}$C, and $^{29}$Si NMR again which showed a slight shift to upfield and a new small unidentified peak at ~−65 in $^{29}$Si NMR was observed, possibly as a result of the water treatment and formation of Si—OH bonds. The NMR data are as follows: Yield: 70% $^1$H NMR (δ, ppm): −0.325 (m), 3.087 (m), 3.160 (s), 3.198 (m), 3.898 (m); $^{29}$Si NMR (δ, ppm): −57.027 (m), −65.703 (m).

D. Synthesis of Delivery Vehicle (PEG400)$_8$T$_8$

Cubic siloxane T$_8$ based delivery vehicles were also synthesized. Octakis(dimethylsiloxy)-T8-Silsesquioxane (T$_8$) (see structure 8 below) is a cubic structure and has 8 Si—H vertices as compared to 4 Si—H vertices present in D$_4$. Wilkinson's catalyst (0.001 g, 0.001 mmol) and Octakis(dimethylsiloxy)-T8-Silsesquioxane (T$_8$) (see structure 8 below; 0.2545 g, 0.25 mmol) were added to a 50 mL schlenk tube equipped with a magnetic stirring bar. The Schlenk tube was degassed and filled with nitrogen three times. Solvent (Benzene, 5 mL) was added, which resulted in a brownish solution. PEG (see structure 1 below; PEG MW 400 Da; 0.8 g, 2 mmol) was added, and the reaction mixture immediately turned yellow and development of a gas (presumably H$_2$) was observed. The reaction mixture was further degassed and filled with nitrogen three more times. The reaction was allowed to continue at 65° C. under a positive nitrogen pressure for 32 hrs. Upon completion, the reaction mixture was a light yellow viscous solution. The solvent was evaporated and the product was analyzed with $^1$H, and $^{29}$Si NMR, which confirmed the formation of desired product (PEG400)$_8$T$_8$ (see structure 9 below). The synthetic reaction is shown in scheme 4.

Scheme 4:
Synthetic route to PEG400 substituted cubic siloxane and idealized structure of the product.

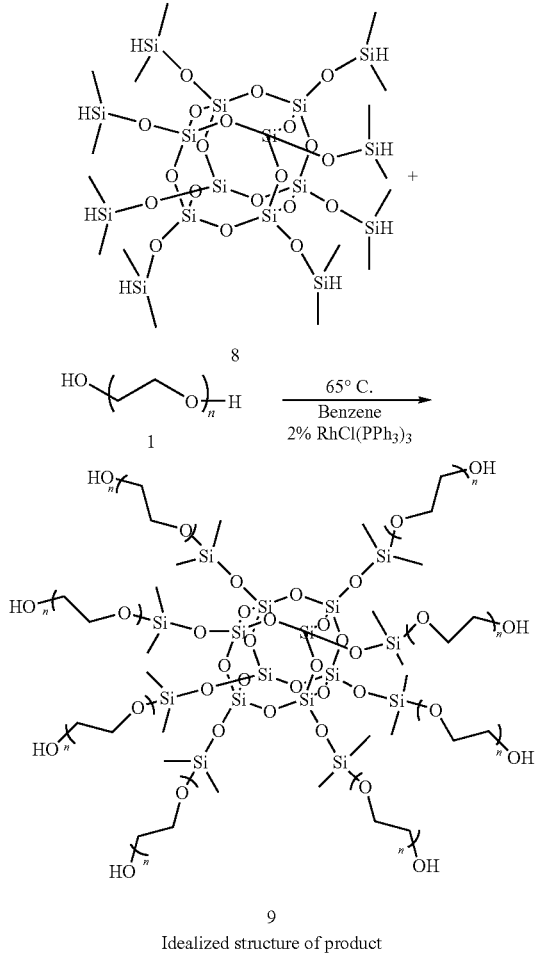

9
Idealized structure of product

The $^1$H, and $^{29}$Si NMR data are summarized as follows: Yield: 96%; $^1$H NMR (δ, ppm): 0.063 (m), 3.485 (m), 3.538 (m), 3.599 (m), 3.733 (m); $^{29}$Si NMR (δ, ppm): −8.192 (m), −109.706 (s)

To separate the catalyst, the reaction mixture was placed in a 250 mL round bottom flask equipped with a magnetic stirring bar. Approximately 30 mL of cyclohexane was added to the flask, and the solution was stirred vigorously for 10 min. Approximately 10 mL of water was added, which resulted in a milky color solution. The solution was vigorously stirred for an additional 20 min and then collected in a separatory funnel and allowed to sit for one hour. The catalyst was separated at the interphase of both layers in form of precipitate. The bottom water layer containing delivery vehicle was separated and centrifuged for 10 min at 9000 rpm to remove any traces of the catalyst. The water was evaporated in a rotary evaporator under vacuum at 95° C. for two hours. The resultant product was a clear viscous solution of delivery vehicle (PEG400)$_8$T$_8$. The product was analyzed with $^1$H and $^{29}$Si NMR again which showed a slight shift to upfield was observed. The NMR data are summarized as follows: Yield:

70%, $^1$H NMR (δ, ppm): 0.062 (m), 3.487 (m), 3.549 (m), 3.600 (m), 3.734 (m); $^{29}$Si NMR (δ, ppm): −9.253 (m), −110.711 (s)

E. Synthesis of Delivery Vehicle (PEG1000)$_8$T$_8$

Wilkinson's catalyst (0.001 g, 0.001 mmol) and Octakis (dimethylsiloxy)-T8-Silsesquioxane (T$_8$) (see structure 8 below; 0.1272 g, 0.125 mmol) were added to a 50 mL schlenk tube equipped with a magnetic stirring bar. The Schlenk tube was degassed and filled with nitrogen three times. Solvent (Benzene, 5 mL) was added, which resulted in a brownish solution. PEG (see structure 4 below; PEG MW 1000 Da; 1.0 g, 1 mmol) was added, and the reaction mixture immediately turned yellow and development of a gas (presumably H$_2$) was observed. The Schlenk tube was further degassed and filled with nitrogen three more times, and the reaction was allowed to continue at 65° C. under a positive nitrogen pressure for 39 hrs. Upon completion, the reaction mixture was a light yellow viscous solution. The solvent was evaporated and the product was analyzed with $^1$H and $^{29}$Si NMR, which confirmed the formation of desired product (PEG1000)$_8$T$_8$ (see structure 10 below). The synthetic reaction is shown in scheme 5.

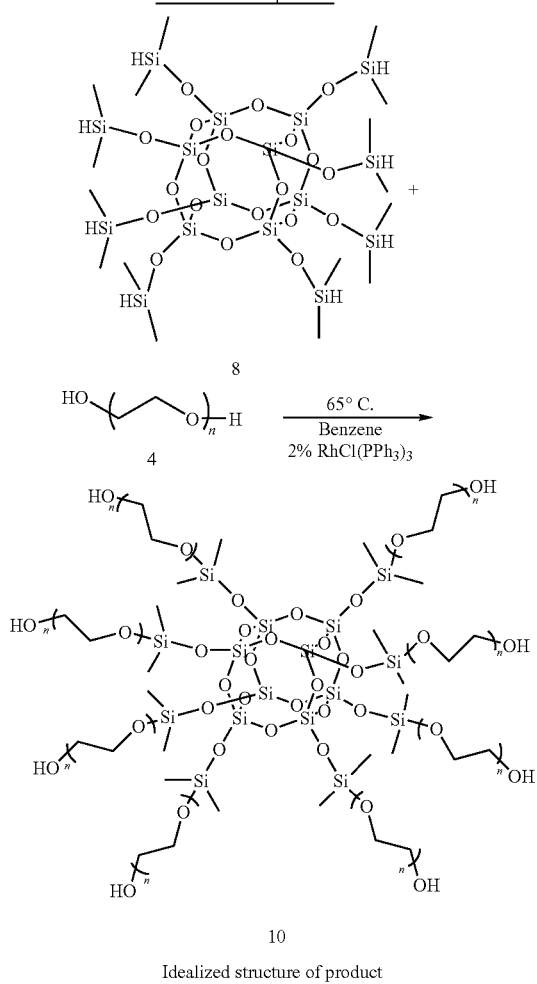

Scheme 5:
Synthetic route to PEG1000 substituted cubic siloxane and idealized structure of the product.

Idealized structure of product

The $^1$H, and $^{29}$Si NMR data are summarized as follows: Yield: 96%; $^1$H NMR (δ, ppm): 0.067 (m), 3.480 (m), 3.535 (m), 3.598 (m), 3.727 (m); $^{29}$Si NMR (δ, ppm): −8.023 (m), −109.680 (s)

The catalyst was separated in a similar fashion as described in preparation of (PEG400)$_8$T$_8$ above. In particular, the reaction mixture was placed in a 250 mL round bottom flask equipped with a magnetic stirring bar. Approximately 30 mL of cyclohexane was added to the flask, and the solution was stirred vigorously for 10 min. Approximately 10 mL of water was added, which resulted in a milky color solution. The solution was vigorously stirred for an additional 20 min and then collected in a separatory funnel and allowed to sit for one hour. The catalyst was separated at the interphase of both layers in form of precipitate. The bottom water layer containing delivery vehicle was separated and centrifuged for 10 min at 9000 rpm to eliminate any traces of the catalyst. The water was evaporated in a rotary evaporator under vacuum at 95° C. for two hours. The resultant was a clear waxy solid of delivery vehicle (PEG1000)$_8$T$_8$. The product was analyzed with $^1$H and $^{29}$Si NMR again which showed a slight shift to upfield and a new small unidentified peak at ~−18 in $^{29}$Si NMR was observed, possibly the result of water treatment and formation of Si—OH bonds. The NMR data are summarized as follows: Yield: 70%, $^1$H NMR (δ, ppm): 0.082 (m), 3.473 (m), 3.529 (m), 3.594 (m), 3.751 (m); $^{29}$Si NMR (δ, ppm): −9.314 (m), −18.752 (m), −110.487 (s)

Example 2

Physical Properties of Drug Delivery Vehicles

The drug delivery vehicles synthesized above in Example 1 were further analyzed.

Transmittance Electron Microscopy Analysis

All of the vehicles formed micelles in appropriate solvents and at specified concentrations. Transmittance Electron Microscopy (TEM) was used to investigate the morphology of the micellar structures. For example, 0.188 gm (0.2 mmol) of (PEG400)$_4$D$_4^M$ was diluted in 20 mL of benzene. After stirring for 10 min to produce a homogenous mixture, one drop of this solution was carefully placed on a formavar coated copper-carbon grid. The solvent was allowed to evaporate at room temperature in the open air for about 10 min. TEM pictures showed a well-defined micellar network with monodispersed particles. The TEM images at 1 micron and 50 nm are shown in FIG. 1.

All of the vehicles of Example 1 were examined by TEM and a similar morphology was found in each case. Slight differences in particle sizes were observed.

Particle Size Analysis by Dynamic Light Scattering

Figure 2:
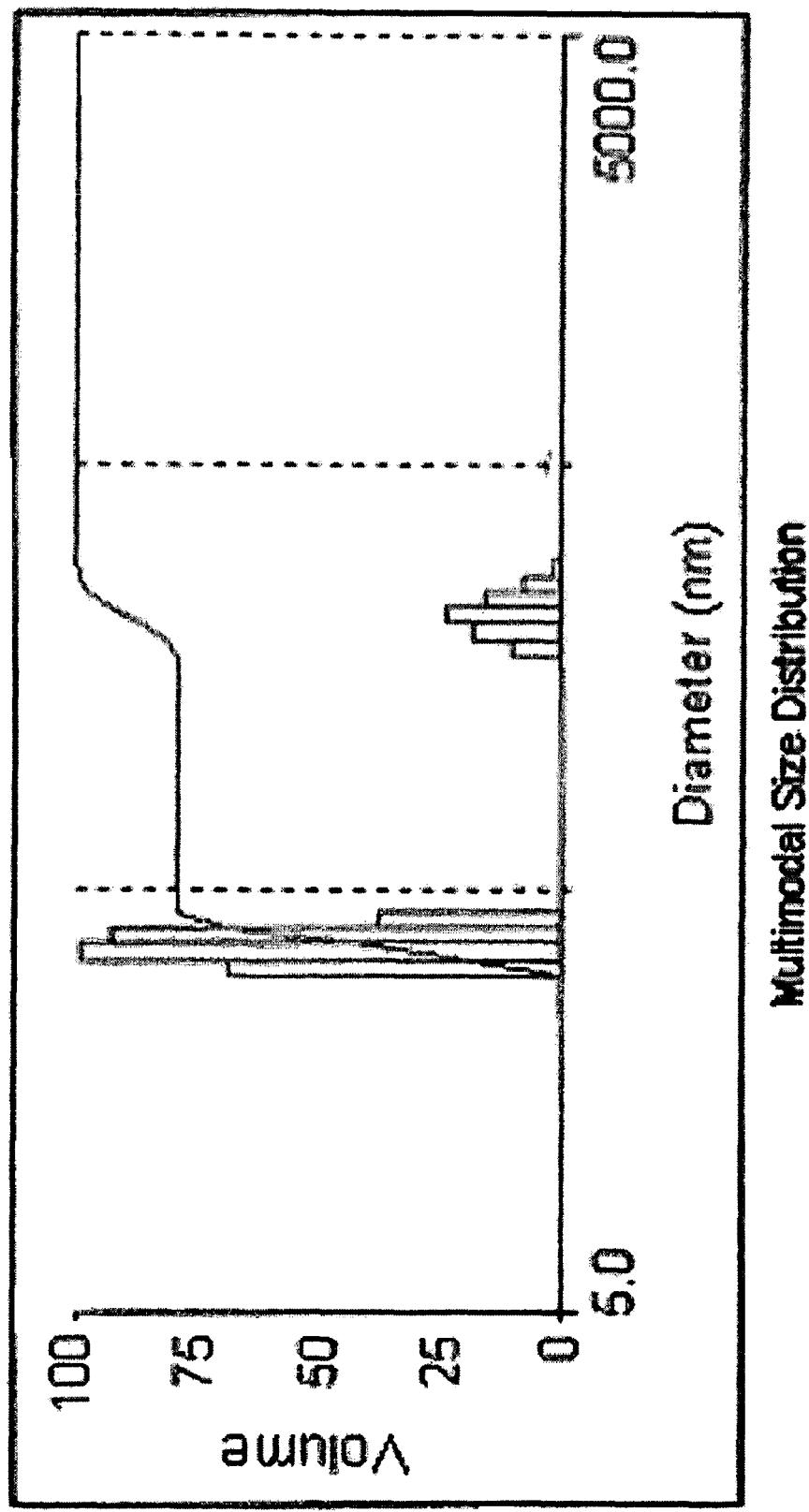
FIG. 2 shows the dynamic light scattering (DLS)-based particle size distribution for a 2.5 mg/ml solution of $(PEG400)_4D_4^M$. Experimental details are provided in Example 2.

Dynamic Light Scattering (DLS) was used to assess nanoparticle formation when the delivery vehicles described above in Example 1 were combined with deionized water to form aqueous suspensions. The DLS-based particle distribution for a 2.5 mg/mL solution of, for example, the delivery vehicle (PEG400)$_4$D$_4^M$ is provided in FIG. 2 and displays a bimodal distribution that is typical for the delivery vehicles of the invention. This concentration of the delivery vehicle is similar to that used in the encapsulation studies described below in Example 3. The DLS data confirm the presence of nanoparticles in the aqueous solutions. The data presented in FIG. 2 can be represented in tabular form by providing the percent total volume for the two main peaks. See Table 1 below:

TABLE 1

Bimodal Distribution of Particle Size of 2.5 mg/mL (PEG400)$_4$D$_4{}^M$ Solution

| Counts/second (cps) | peak 1 (particle size; nm) | % | peak 2 (particle size; nm) | % |
|---|---|---|---|---|
| 1100k | 35 | 80 | 215 | 20 |

*Counts/second (cps) is a relative measure of the number of particles detected by the DLS instrument.

The particle size and distribution of a cisplatin/(PEG400)$_4$D$_4{}^M$ solution (i.e., encapsulated cisplatin) was also analyzed by DLS. The results are summarized in Table 2.

TABLE 2

Particle Size and Distribution of (PEG400)$_4$D$_4{}^M$ +/− Cisplatin

| Sample | cps | peak 1 (particle size; nm) | % | peak 2 (particle size; nm) | % |
|---|---|---|---|---|---|
| Delivery vehicle + cisplatin (with sonication for 60 minutes) | 3.9 M | 183 | 97 | 2500 | 3 |
| Delivery vehicle + cisplatin (at time = 16 hours) | 3.8 M | 74 | 50 | 340 | 50 |
| Delivery vehicle alone (at time = 90 days) | 2.9 M | 64 | 68 | 218 | 32 |
| Delivery vehicle + cisplatin (at time = 90 days) | 3.0 M | 25 | 90 | 190 | 10 |

Other delivery vehicles, including some not described above, were synthesized and assayed in aqueous solution form using DLS for their ability to form nanoparticles. The results of these studies are summarized below in Table 3.

TABLE 3

Particle Size and Distribution of Various Multi-Arm Siloxane-based Delivery Vehicles with 60 Minute Sonication

| Sample | cps | peak 1 (particle size; nm) | % | peak 2 (particle size; nm) | % |
|---|---|---|---|---|---|
| (PEG400)$_5$D$_5$ (10 mg/mL) | 2.1 M | 96 | 35 | 424 | 65 |
| (PEG methyl ether 350)$_4$D$_4$ (5 mg/mL) | 4.0 M | 71 | 48 | 364 | 52 |
| (PEG methyl ether 550)$_4$D$_4$ (5 mg/mL) | 2.3 M | 39 | 85 | 176 | 15 |
| (PEG400)$_8$T$_8$ (5 mg/mL) | 308k | 121 | 92 | 520 | 8 |

Example 3

Encapsulation of Therapeutic Agents into Drug Delivery Vehicles

Therapeutic agents (i.e., cisplatin and paclitaxel) were encapsulated into the drug delivery vehicles described above in Examples 1 and 2. Exemplary methods for encapsulation of these drugs and the results obtained are described below.

A. Encapsulation of Cisplatin

Figure 3:
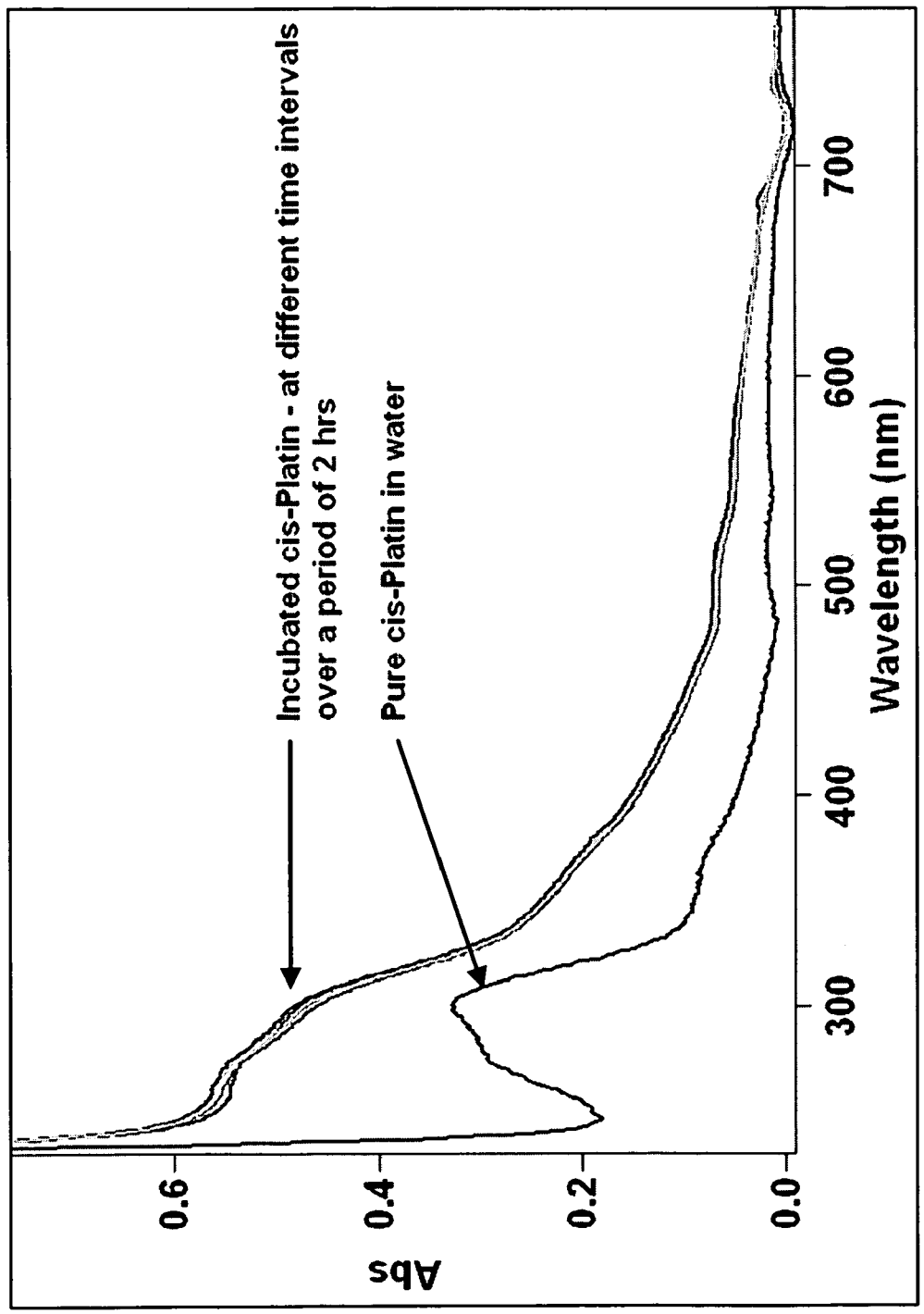
FIG. 3 provides the UV-visible (UV-vis) spectra for unencapsulated cisplatin and cisplatin encapsulated in $(PEG400)_4D_4^M$. Experimental details are provided in Example 2.

1. Encapsulation of Cisplatin in (PEG400)$_4$D$_4{}^M$ 5 mg of cisplatin was placed in a glass vial, and water (10 mL) was then added to the vial. The vial was sonicated in a Bransonic Ultrasonic Cleaner (115 v, 50/60 HZ, 40 Hz transducer) for about 5 min to completely dissolve the cisplatin. 50 mg of the delivery vehicle (PEG400)$_4$D$_4{}^M$ was placed in another vial and water (10 mL) was added to it. Upon shaking, the polymer dissolved immediately. The cisplatin solution was added to the vehicle solution drop-wise with simultaneous sonication. After the mixing was completed, a UV-vis spectrum was recorded. The solution was further sonicated for 1 hr and periodically monitored with UV-vis spectroscopy to examine the incubation process. After 1 hr, sonication was stopped and the incubation was allowed to continue at room temperature without shaking. For reference, another solution of pure cisplatin was prepared at a similar concentration. A UV-vis spectrum was recorded for the cisplatin solution alone and was compared with that of the cisplatin/delivery vehicle solution. A significant increase in absorbance was observed in peaks associated with cisplatin in the pure cisplatin solution and in the cisplatin/delivery vehicle solution. This change in the peak position was interpreted as an indication of the encapsulation of cisplatin in the delivery vehicle (PEG400)$_4$D$_4{}^M$. The UV-vis spectroscopy results are provided in FIG. 3.

Figure 4:
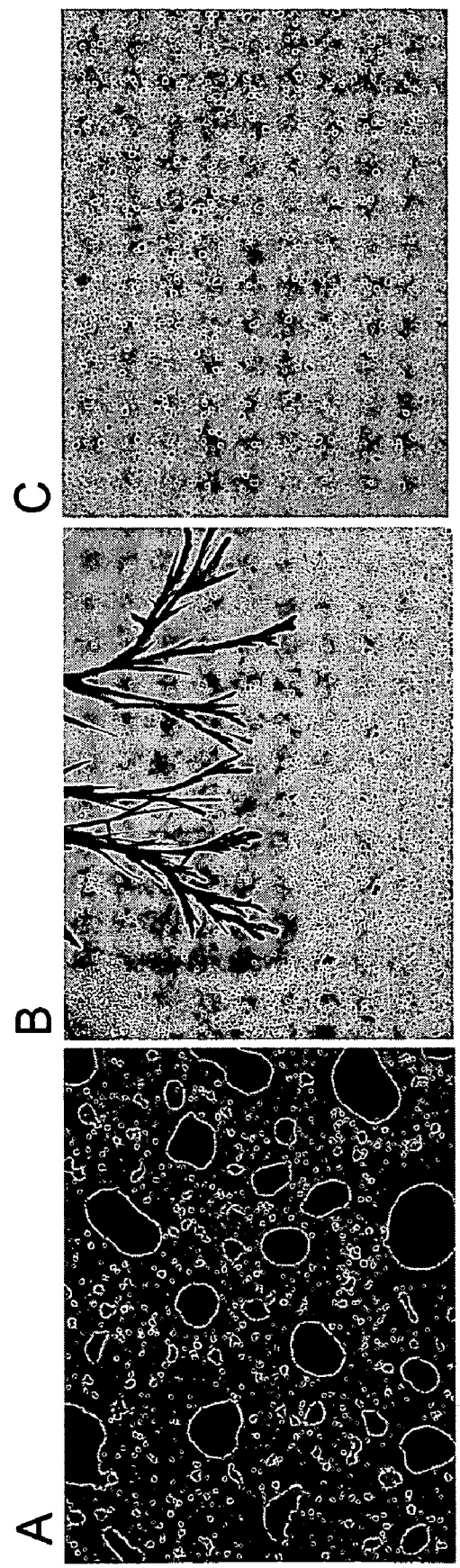
FIG. 4 provides microscopy images of $(PEG400)_4D_4^M$ alone (A), pure, unencapsulated cisplatin (B), and cisplatin encapsulated in $(PEG400)_4D_4^M$ (C). Experimental details are provided in Example 2.

The cisplatin/delivery vehicle samples were also examined under a microscope to further investigate the encapsulation. Specifically, a comparison was made between encapsulated and un-encapsulated cisplatin. One drop of each solution was placed on a separate glass slide and water was allowed to evaporate at room temperature in open air. After complete evaporation of water, dry sample spots were covered and sealed by cover slides, and both slides were examined under microscope. Un-encapsulated cisplatin formed crystals as the water was evaporating, whereas no such crystal formation was observed with the cisplatin/delivery vehicle sample, further suggesting that the cisplatin was encapsulated in the delivery vehicle. The microscopy results are shown in FIGS. 4A, B, and C.

Figure 5:
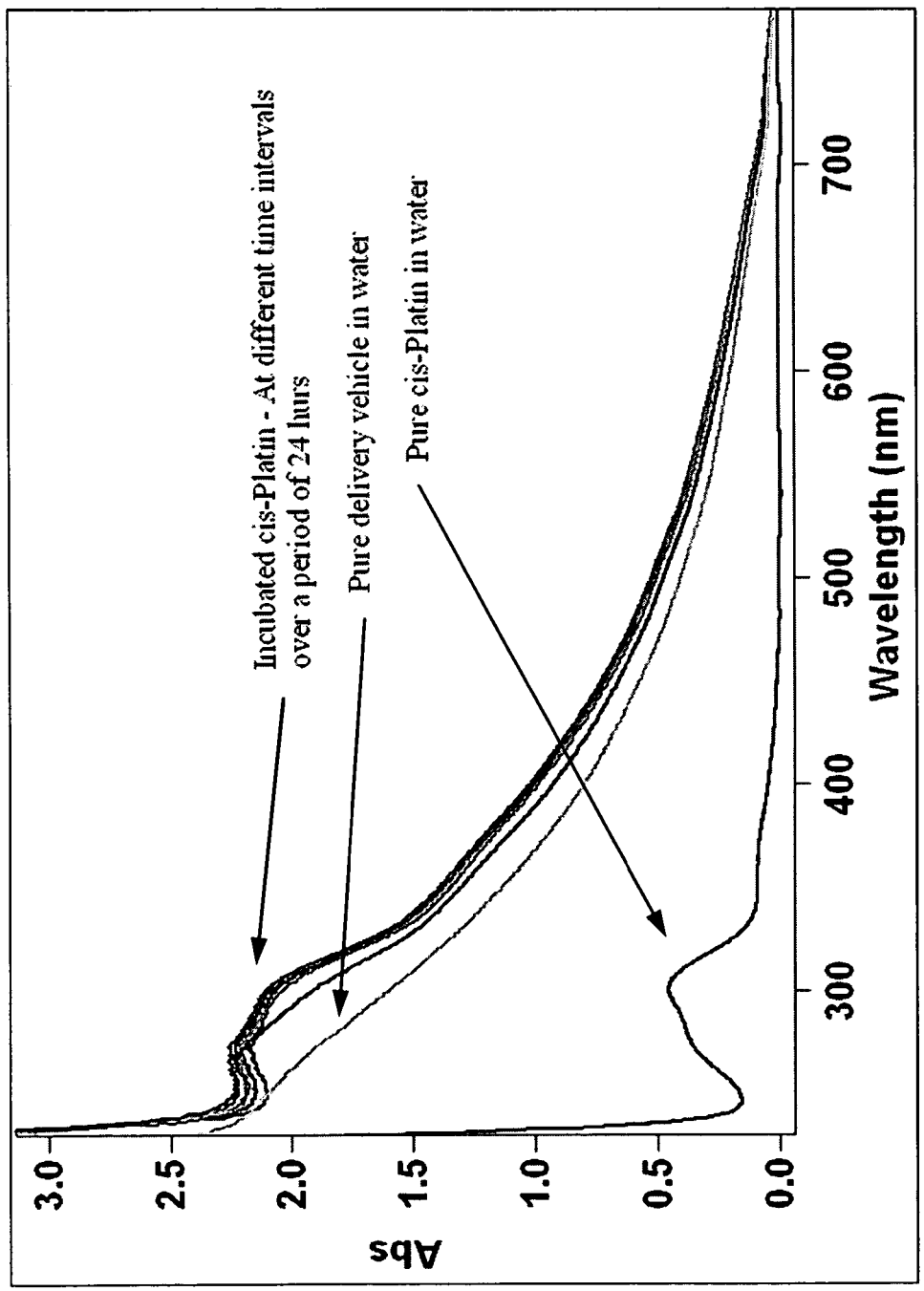
FIG. 5 provides the UV-visible (UV-vis) spectra for unencapsulated cisplatin and cisplatin encapsulated in $(PEG1000)_4D_4^M$ at different time intervals over a period of 24 hours. Experimental details are provided in Example 2.
Figure 6:
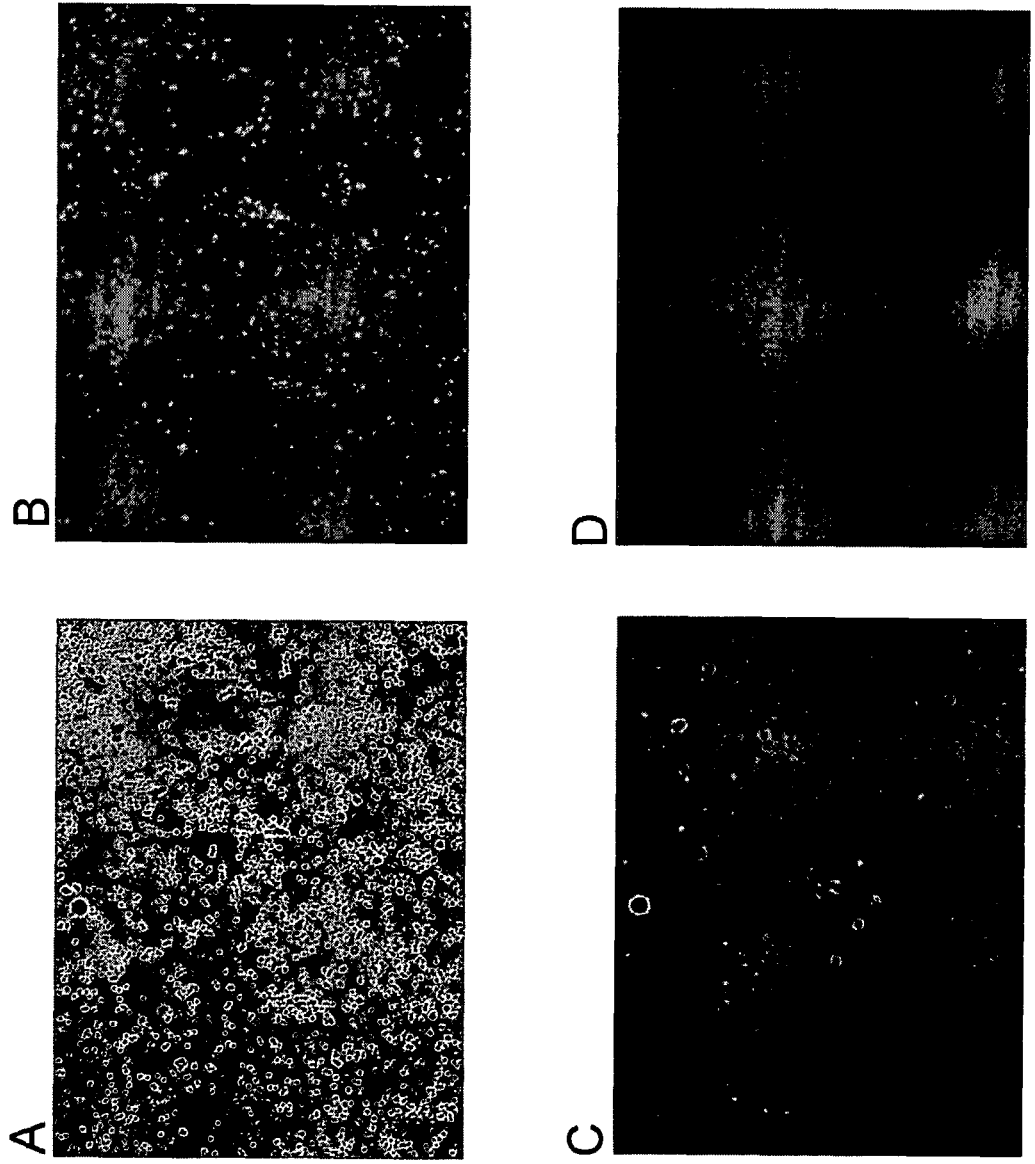
FIG. 6 shows microscopy images of unencapsulated paclitaxel in the absence (A) and presence (B) of fluorescent light. Paclitaxel encapsulated in $(PEG400)_4D_4^M$ is also shown in the absence (C) and presence (D) of fluorescent light. Experimental details are provided in Example 3.

2. Encapsulation of Cisplatin in (PEG1000)$_4$D$_4{}^M$ 5 mg of cisplatin was placed in a glass vial and water (2.5 mL) was added to it. The vial was sonicated in a Bransonic Ultrasonic Cleaner (115 v, 50/60 HZ, 40 Hz transducer) for about 5 min to achieve maximum solubility of cisplatin. In another vial, 100 mg of the delivery vehicle (PEG1000)$_4$D$_4{}^M$ was placed and water (2.5 mL) was added to it. The vial was sonicated for about 2 min to dissolve vehicle. The cisplatin solution was added to the delivery vehicle solution drop-wise with sonication. After the mixing was completed, a UV-vis spectrum was recorded. The solution was further sonicated for 60 min and periodically monitored with UV-vis spectroscopy to examine the incubation process. The sonication was stopped after 60 min and the solution was periodically monitored with UV-vis spectroscopy for the next 24 hrs. For reference, two samples of cisplatin and delivery vehicle alone were prepared at similar concentrations. UV-vis spectra were recorded for both reference solutions separately. A significant increase in absorbance was observed in peaks associated with cisplatin in the pure cisplatin solution and in the cisplatin/delivery vehicle solution (data not shown). This change in absorbance is indicative of encapsulation of cisplatin into the delivery vehicle (PEG1000)$_4$D$_4{}^M$. See FIG. 5.

The cisplatin/delivery vehicle samples were also examined under a microscope to further investigate the encapsulation. A comparison was made between encapsulated and un-encapsulated cisplatin. One drop of each solution was placed on a separate glass slide and water was allowed to evaporate at room temperature in the open air. After complete evaporation of the water, dry sample spots were covered and sealed by cover slides, and both slides were examined under microscope (data not shown). Un-encapsulated cisplatin formed crystals as the water was evaporating, whereas no such crystal formation was observed with the cisplatin/delivery vehicle sample, further suggesting that the cisplatin was encapsulated in the delivery vehicle.

3. Encapsulation of Cisplatin in $(PEG400)_5D_5^M$ 5 mg of cisplatin was placed in a glass vial and water (10 mL) was added to it. The vial was sonicated in a Bransonic Ultrasonic Cleaner (115 v, 50/60 HZ, 40 Hz transducer) for about 5 min to achieve maximum solubility of cisplatin. In another similar vial, 100 mg of the delivery vehicle $((PEG400)_5D_5^M)$ was placed and water (5 mL) was added to it. The vial was sonicated for about 2 min to dissolve vehicle. The cisplatin solution was added to vehicle solution dropwise with sonication. After the mixing was completed, a UV-vis spectrum was recorded. The solution was further sonicated for 60 min and periodically monitored with UV-vis spectroscopy to examine the incubation process. Sonication was stopped after 60 min and the solution was periodically monitored with UV-vis spectroscopy for the next 24 hrs. For reference, two samples of cisplatin and delivery vehicle alone were prepared at similar concentrations. UV-vis spectra were recorded for both reference solutions separately. A significant increase in absorbance was observed in peaks associated with cisplatin in the pure cisplatin solution and in the cisplatin/delivery vehicle solution. This change in the peak position is indicative of encapsulation of cisplatin into the delivery vehicle $(PEG400)_5D_5^M$ (data not shown).

The cisplatin/delivery vehicle samples were also examined under a microscope to further investigate the encapsulation. A comparison was made between encapsulated and un-encapsulated cisplatin. One drop of each solution was placed on a separate glass slide and water was allowed to evaporate at room temperature in the open-air. After complete evaporation of water, dry sample spots were covered and sealed by cover slides, and both slides were examined under microscope (data not shown). Un-encapsulated cisplatin formed crystals as the water was evaporating, whereas no such crystal formation was observed with the cisplatin/delivery vehicle sample, further suggesting that the cisplatin was encapsulated in the delivery vehicle.

B. Encapsulation of Paclitaxel

1. Encapsulation of Paclitaxel in $(PEG400)_4D_4^M$ 5 mg of paclitaxel was placed in a glass vial, and 10 mL of ethanol was added. The vial was sonicated in a Bransonic Ultrasonic Cleaner (115 v, 50/60 HZ, 40 Hz transducer) for approximately two minutes to completely dissolve the paclitaxel. 50 mg of the delivery vehicle $(PEG400)_4D_4^M$ was placed in a separate glass vial 10 mL of ethanol was added. Upon shaking, the delivery vehicle dissolved readily. UV-vis spectra were recorded for both solutions separately. The paclitaxel solution was slowly added to the delivery vehicle solution. After complete addition of the paclitaxel solution to the vehicle solution, the vial was gently shaken and a UV-vis spectrum was recorded. The solution was left at room temperature without shaking and was further monitored with UV-vis spectroscopy periodically to examine the encapsulation process. Two reference samples of paclitaxel and delivery vehicle alone were prepared at similar concentrations in ethanol separately and were also monitored with UV-vis spectroscopy. In contrast to the results observed with the cisplatin solutions, UV-vis spectroscopy was ineffective at monitoring encapsulation of paclitaxel (data not shown). Accordingly, further studies were performed to confirm encapsulation.

To verify the encapsulation, samples were examined under the microscope and a comparison was made between the paclitaxel solution alone and the paclitaxel/delivery vehicle solution. In particular, one drop of each solution was placed on a separate glass slide and the ethanol was allowed to evaporate at room temperature in the open-air. After complete evaporation of the ethanol, dry sample spots were covered and sealed by cover slides and both slides were examined under microscope. It was observed that un-encapsulated paclitaxel shows fluorescence activity when exposed to fluorescent light. In contrast, when the paclitaxel/delivery vehicle solution (i.e., encapsulated paclitaxel) was observed under the same fluorescent light, no fluorescence of the particles was observed, suggesting that the encapsulated paclitaxel is in the core of the micelles of the delivery vehicles, thereby diminishing its fluorescence activity. The microscopy results are provided in FIGS. 6A-D.

2. Encapsulation/Incubation of Paclitaxel in $(PEG1000)_4D_4^M$ 10 mg of paclitaxel was place in a glass vial and ethanol (2.5 mL) was added. The vial was sonicated in a Bransonic Ultrasonic Cleaner (115 v, 50/60 HZ, 40 Hz transducer) for 2 minutes to completely dissolve the paclitaxel. 200 mg of the delivery vehicle $((PEG1000)_4D_4^M)$ was placed in a separate vial and Ethanol (2.5 mL) was added. The delivery vehicle was dissolved in ethanol by sonicating for 2 min. The paclitaxel solution was slowly added to the delivery vehicle solution. After the mixing was completed, the vial was gently shaken and a UV-vis spectrum was recorded. The solution was left at room temperature without shaking and was further monitored with UV-vis spectroscopy periodically to examine the encapsulation process. Two reference samples of paclitaxel and the delivery vehicle alone were prepared separately at similar concentrations in ethanol, and UV-vis spectra were recorded for both reference solutions. As previously noted, UV-vis spectroscopy was not effective at monitoring encapsulation of paclitaxel (data not shown), and, therefore, the samples were examined under microscope for evidence of encapsulation.

For microscopic analysis, one drop of each solution (i.e., paclitaxel alone paclitaxel/delivery vehicle solutions) and was placed on a separate glass slide. The ethanol was allowed to evaporate at room temperature in the open-air. After complete evaporation of the ethanol, dry sample spots were covered and sealed by cover slides and both slides were examined under the microscope. As described above with the paclitaxel/ $(PEG400)_4D_4^M$ solution, it was observed that un-encapsulated paclitaxel shows fluorescence activity when exposed to fluorescent light. In contrast, when the paclitaxel/delivery vehicle solution (i.e., encapsulated paclitaxel) was observed under the same fluorescent light, no fluorescence of the particles was observed, suggesting that the encapsulated paclitaxel is in the core of the micelles of the delivery vehicles, thereby diminishing its fluorescence activity (data not shown).

3. Encapsulation/Incubation of Paclitaxel in $(PEG400)_5D_5^M$ 10 mg of paclitaxel was placed in a glass vial and ethanol (2.5 mL) was added. The vial was sonicated in a Bransonic Ultrasonic Cleaner (115 v, 50/60 HZ, 40 Hz transducer) for 2 minutes to completely dissolve the paclitaxel. 200 mg of the delivery vehicle $(PEG400)_5D_5^M$ was placed in a separate vial and 2.5 mL of ethanol added. Upon shaking, the polymer dissolved immediately. The paclitaxel solution was slowly added to delivery vehicle solution. After mixing was completed, the vial was gently shaken and a UV-vis spectrum was recorded. The Solution was further monitored with UV-vis spectroscopy periodically to examine the encapsulation process. Two reference samples of paclitaxel and delivery vehicle alone were prepared at similar concentrations in 5 mL of ethanol each. Again, UV-vis spectroscopy was not effective at monitoring encapsulation of paclitaxel in the delivery vehicles.

For microscopic analysis, one drop of each solution (i.e., paclitaxel alone paclitaxel/delivery vehicle solutions) and was placed on a separate glass slide. The ethanol was allowed to evaporate at room temperature in the open-air. After complete evaporation of the ethanol, dry sample spots were covered and sealed by cover slides and both slides were examined under the microscope. As described above with the paclitaxel/(PEG400)$_4$D$_4^M$ solution, it was observed that un-encapsulated paclitaxel shows fluorescence activity when exposed to fluorescent light. In contrast, when the paclitaxel/delivery vehicle solution (i.e., encapsulated paclitaxel) was observed under the same fluorescent light, no fluorescence of the particles was observed, suggesting that the encapsulated paclitaxel is in the core of the micelles of the delivery vehicles, thereby diminishing its fluorescence activity (data not shown).

Several samples of encapsulated cisplatin and paclitaxel were prepared using different concentrations and with different delivery vehicles. Similar results were obtained as those described above.

Example 4

Release of Cisplatin from Drug Delivery Vehicles

A drug release time study was performed on encapsulated cisplatin (i.e., cisplatin/delivery vehicle) to assess the time for complete release of the encapsulated drug from the delivery vehicle. UV-vis spectroscopy was used to monitor the change in absorbance in peaks associated with cisplatin over time. The cisplatin time release study procedures and data are summarized below.

5 mg of cisplatin was placed in a glass vial and 10 mL of water (10 mL) added. The vial was sonicated in a Bransonic Ultrasonic Cleaner (115 v, 50/60 HZ, 40 Hz transducer) for about 5 min to completely dissolve the cisplatin. 50 mg of the delivery vehicle (PEG400)$_4$D$_4^M$ was placed in a separate vial and 10 mL of water added. Upon shaking, the polymer dissolved immediately. The cisplatin solution was added to the delivery vehicle solution drop-wise with sonication. After the mixing was complete, a UV-vis spectrum was recorded. The solution was further sonicated for 1 hr and monitored with UV-vis spectroscopy at intervals of 10 min to examine the encapsulation process. After 1 hr, sonication was stopped and incubation was allowed to continue at room temperature without shaking. UV-vis spectra were recorded at 20 min intervals for one hr, followed by 3 hours intervals for the next 24 hrs. After 24 hrs, UV-vis spectra were recorded at random intervals for several days to monitor the release time of the cisplatin. For reference, another solution of pure cisplatin was prepared at a similar concentration, and UV-vis spectra were recorded for the un-encapsulated cisplatin solution at similar intervals as with the encapsulated cisplatin solution. In about 200 hours (~9 days), the absorbance of the encapsulated cisplatin solution dropped to the same level as that of the un-encapsulated cisplatin solution. This was viewed as the complete release of encapsulated cisplatin from the vehicle. A summary of the absorbance of both solutions at various time points is provided in Table 4. All data provided in Table 4 were collected at a wavelength of 300 nm.

TABLE 4

UV-vis Spectra Results of Un-encapsulated and Encapsulated cisplatin at Various Time Points

| Time (hrs) | Absorbance (encapsulated cisplatin) | Absorbance (un-encapsulated cisplatin |
|---|---|---|
| 0.00 | 0.54 | 0.18 |
| 0.17 | 0.56 | 0.17 |
| 0.33 | 0.56 | 0.16 |
| 0.50 | 0.57 | 0.16 |
| 0.67 | 0.58 | 0.16 |
| 0.83 | 0.58 | 0.16 |
| 1.00 | 0.59 | 0.16 |
| 1.33 | 0.59 | 0.16 |
| 1.67 | 0.58 | 0.16 |
| 2.00 | 0.57 | 0.16 |
| 3.00 | 0.57 | 0.16 |
| 21.00 | 0.56 | 0.15 |
| 24.00 | 0.56 | 0.15 |
| 42.00 | 0.55 | 0.15 |
| 45.00 | 0.55 | 0.15 |
| 72.00 | 0.49 | 0.15 |
| 88.00 | 0.48 | 0.15 |
| 120.00 | 0.47 | 0.15 |
| 150.00 | 0.15 | 0.15 |
| 174.00 | 0.15 | 0.15 |
| 230.00 | 0.15 | 0.15 |

Example 5

Analysis of Drug Delivery Vehicles By Fluorescence Microscopy

The drug delivery vehicles described in the Examples above (i.e., solutions comprising the multi-arm siloxane-based molecules) were further analyzed using fluorescence microscopy. In particular, a fluorescent dye was used in place of a therapeutic agent in order to monitor encapsulation. The delivery vehicle was dissolved in water and the fluorescent dye added. After shaking for about 5 min, the sample was allowed to sit for one hour in order to achieve encapsulation of the dye particles in the delivery vehicle molecules. One drop of the water solution was deposited on a glass slide and was monitored under a microscope, with and without a fluorescence filter.

Figure 7:
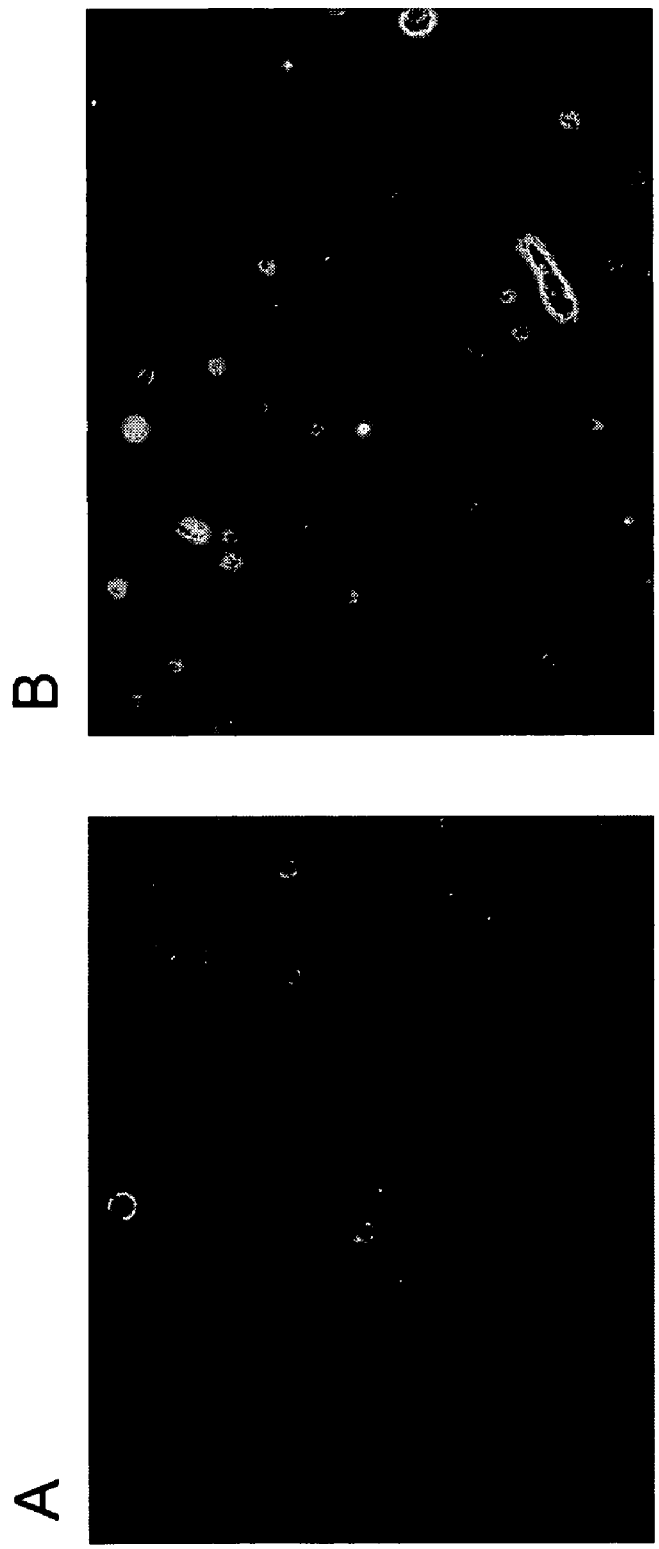
FIG. 7 provides fluorescence microscopy images of fluorescent dye encapsulated in a multi-arm siloxane-based molecule delivery vehicle. The images were generated at 100× magnification and without (A) and with (B) a fluorescence filter. Experimental details are provided in Example 5.

Without the fluorescence filter, the particles/micelles of the delivery vehicle were visible as goblets in a water solution. Upon turning the fluorescence filter on, only the vehicle particles were visible, whereas water background was blank. This result indicates that all of the dye molecules were encapsulated in the delivery vehicle. No dye was observed in the water, further indicating complete encapsulation in the delivery vehicle. See FIG. 7.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A multi-arm siloxane-based molecule for use as a drug delivery vehicle comprising a central core molecule that comprises a cyclic siloxane and a plurality of arms attached to the central core molecule, wherein each arm comprises an organic moiety, and wherein one or more of insulin, cisplatin, or paclitaxel is encapsulated in the molecule.

2. The multi-arm siloxane-based molecule of claim 1, wherein the central core molecule is tetramethylcyclotetrasiloxane or pentamethylcyclopentasiloxane.

3. The multi-arm siloxane-based molecule of claim 1, wherein the central core molecule is attached to about 3 to about 10 arms.

4. The multi-arm siloxane-based molecule of claim 3, wherein the central core molecule is attached to about 4 to about 8 arms.

5. The multi-arm siloxane-based molecule of claim 1, wherein the organic moiety of each arm comprises a polyethylene glycol (PEG).

6. The multi-arm siloxane-based molecule of claim 5, wherein the PEG has a molecular weight of about 400 Da to about 1500 Da.

7. The multi-arm siloxane-based molecule of claim 5, wherein the PEG has a molecular weight of about 400 Da.

8. The multi-arm siloxane-based molecule of claim 5, wherein the PEG has a molecular weight of about 1000 Da.

9. The multi-arm siloxane-based molecule of claim 5, wherein the PEG is selected from the group consisting of PEG-tetrahydrofurfuryl ether, PEG-methyl ether 350, and PEG-methyl ether 550.

10. The multi-arm siloxane-based molecule of claim 1, wherein the molecule is selected from the group consisting of $(PEG400)_4D_4^M$, $(PEG1000)_4D_4^M$, $(PEG400)_5D_5^M$, $(PEG-THF\ ether)_4D_4^M$, $DA_4D_4^M$, $BE_4D_4^M$, $[PEGMetEt(350)]_4D_4^M$, and $[PEGMetEt(550)]_4D_4^M$.

11. A composition comprising a plurality of the multi-arm siloxane-based molecule of claim 1.

12. The composition of claim 11, wherein the plurality of multi-arm siloxane based molecules form a micellar structure in a solution.

13. A pharmaceutical composition comprising the multi-arm siloxane-based molecule of claim 1 and a pharmaceutically acceptable carrier.

14. A pharmaceutical composition comprising:
a multi-arm siloxane-based molecule for use as a drug delivery vehicle comprising a central core molecule that comprises a cyclic siloxane and a plurality of arms attached to the central core molecule, wherein each arm comprises a PEG selected from the group consisting of PEG-tetrahydrofurfuryl ether, PEG-methyl ether 350, and PEG-methyl ether 550;
a therapeutic agent selected from the group consisting of anticancer agents, diabetes-controlling agents, antibiotics, antifungal agents, antiviral agents, anti-inflammatory drugs, migraine drugs, anti-anxiety agents, hormones, growth factors, steroidal agents, cardiovascular agents, and combinations thereof; and
a pharmaceutically acceptable carrier.

15. The multi-arm siloxane-based molecule of claim 14, wherein the central core molecule is tetramethylcyclotetrasiloxane or pentamethylcyclopentasiloxane.

16. The multi-arm siloxane-based molecule of claim 14, wherein the central core molecule is attached to about 3 to about 10 arms.

17. The multi-arm siloxane-based molecule of claim 14, wherein the central core molecule is attached to about 4 to about 8 arms.

18. A composition comprising a plurality of the multi-arm siloxane-based molecule of claim 14.

19. A pharmaceutical composition comprising the multi-arm siloxane-based molecule of claim 14 having at least one therapeutic went encapsulated within the molecule and a pharmaceutically acceptable carrier.

20. A pharmaceutical composition comprising
a plurality of siloxane-based molecules for use as a drug delivery vehicle comprising a central core molecule that comprises a cyclic siloxane and a plurality of arms attached to the central core molecule, wherein each arm comprises an organic moiety, wherein the plurality of multi-arm siloxane based molecules forms a micellar structure in a solution;
a therapeutic agent selected from the group consisting of anticancer agents, diabetes-controlling agents, antibiotics, antifungal agents, antiviral agents, anti-inflammatory drugs, migraine drugs, anti-anxiety agents, hormones, steroidal agents, cardiovascular agents, and combinations thereof; and
a pharmaceutically acceptable carrier.

* * * * *